(12) United States Patent
Sliwa

(10) Patent No.: US 9,352,174 B2
(45) Date of Patent: May 31, 2016

(54) ABLATION SYSTEM WITH BLOOD LEAKAGE MINIMIZATION AND TISSUE PROTECTIVE CAPABILITIES

(75) Inventor: John W. Sliwa, Los Altos Hills, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1920 days.

(21) Appl. No.: 12/648,797

(22) Filed: Dec. 29, 2009

(65) Prior Publication Data

US 2010/0168624 A1 Jul. 1, 2010

Related U.S. Application Data

(60) Provisional application No. 61/141,379, filed on Dec. 30, 2008.

(51) Int. Cl.
| | | |
|---|---|---|
| *A61N 7/02* | (2006.01) | |
| *A61B 7/00* | (2006.01) | |
| *A61B 6/12* | (2006.01) | |
| *A61B 18/14* | (2006.01) | |
| *A61B 18/18* | (2006.01) | |
| *A61B 18/24* | (2006.01) | |
| *A61B 17/00* | (2006.01) | |
| *A61B 18/00* | (2006.01) | |
| *A61B 19/00* | (2006.01) | |

(52) U.S. Cl.
CPC . *A61N 7/022* (2013.01); *A61B 7/00* (2013.01); *A61B 6/12* (2013.01); *A61B 18/1492* (2013.01); *A61B 18/1815* (2013.01); *A61B 18/24* (2013.01); *A61B 2017/00084* (2013.01); *A61B 2017/00106* (2013.01); *A61B 2018/00011* (2013.01); *A61B 2018/1861* (2013.01); *A61B 2019/4018* (2013.01); *A61B 2019/4081* (2013.01)

(58) Field of Classification Search
CPC .......... A61B 18/1492; A61B 18/1815; A61B 18/24; A61B 2017/00084; A61B 2017/00106; A61B 2018/00011; A61B 2018/1861; A61B 2019/4018; A61B 6/12; A61B 7/00; A61N 7/022

See application file for complete search history.

(56) References Cited

U.S. PATENT DOCUMENTS

| | | | |
|---|---|---|---|
| 6,635,054 B2 | 10/2003 | Fjield et al. | |
| 2002/0019627 A1* | 2/2002 | Maguire et al. | 606/27 |
| 2004/0176757 A1 | 9/2004 | Sinelnikov et al. | |
| 2005/0288666 A1* | 12/2005 | Bertolero et al. | 606/41 |
| 2006/0106375 A1* | 5/2006 | Werneth et al. | 606/32 |
| 2009/0326609 A1* | 12/2009 | Doron | 607/60 |

FOREIGN PATENT DOCUMENTS

WO 2005102199 A1 11/2005

* cited by examiner

*Primary Examiner* — Amanda Lauritzen Moher
(74) *Attorney, Agent, or Firm* — Dykema Gossett, PLLC.

(57) ABSTRACT

An ablation system is provided that includes an ablating device and a probe. The probe is configured to be positioned in close proximity to a region of non-targeted tissue proximate an ablation site of targeted tissue. The probe includes an elongate shaft having proximal and distal ends, with a handle disposed at the proximal end thereof and a tissue protecting apparatus disposed at the distal end thereof. The ablating device includes an elongate shaft having proximal and distal ends, with a handle mounted at the proximal end thereof and an ablation element mounted at the distal end thereof. The ablation element includes an ultrasound transducer and an inflatable balloon surrounding the ultrasound transducer. The balloon includes a layer of gel disposed on its outer surface.

25 Claims, 10 Drawing Sheets

ABLATION SYSTEM WITH BLOOD LEAKAGE MINIMIZATION AND TISSUE PROTECTIVE CAPABILITIES

CROSS REFERENCE TO RELATED APPLICATIONS

This application claims the benefit of U.S. Provisional Patent Application Ser. No. 61/141,379 filed Dec. 30, 2008 and entitled "An Ablation System with Blood Leakage Compensation and Temperature Monitoring/Management Capabilities," which is incorporated herein by reference in its entirety.

BACKGROUND OF THE INVENTION a. Field of the Invention

The present invention relates generally to medical systems for performing therapeutic functions, such as, for example, ablation procedures. More particularly, the present invention relates to an ablation system that includes blood leakage minimization and/or tissue protective capabilities.

b. Background Art

It is known to use minimally invasive surgical devices or ablating tools to perform ablation procedures in, for example, the heart. For instance, in treating a condition known as atrial fibrillation, it is known to advance an ablating tool through the vasculature of a patient to a desired location, and to then thermally ablate tissue within, for example, an ostium (OS) connecting a pulmonary vein to the heart, or to ablate the tissue within the heart surrounding the OS.

One example of a type of tool known in the art to perform such procedures is a catheter-based ablating device such as that or those described in U.S. Pat. No. 6,635,054 entitled "Thermal Treatment Methods and Apparatus with Focused Energy Application," U.S. Patent Publication No. 2004/0176757 entitled "Cardiac Ablation Devices," and International Publication No. WO 2005/102199 entitled "Ablation Devices with Sensor Structures." These known devices generally include, among other components, an elongate shaft having a proximal end, a distal end, and a longitudinal axis extending therebetween. The devices further include an ablation element mounted at or near the distal end of the elongate shaft. In at least one such device, the ablation element comprises a pair of inflatable balloons that share a common wall therebetween, with one of the balloons being disposed proximally of the other balloon. The balloons are configured to have a collapsed condition and an expanded condition, and are configured such that one is liquid or fluid inflated and one is gas inflated. The ablation element further includes an ultrasound transducer mounted or otherwise disposed within the distally disposed balloon that is configured to emit high intensity ultrasonic waves radially outwardly into the liquid or fluid within the balloon with respect to the longitudinal axis of the elongate shaft. The ultrasonic waves have the strength and intensity to burn or ablate tissue after they are reflectively focused forward (more distally onto the OS interior) by the reflectively curved fluid/gas interface defined, in part, by the common wall shared by the two overlying balloons.

In operation, once such an ablating device is positioned in a desired location within the patient's anatomy (e.g., in a pulmonary vein OS), the balloons are respectively inflated with saline (inner balloon) and carbon dioxide gas (outer balloon). The ultrasound transducer is then selectively activated to emit ablating energy (e.g., intense ultrasonic waves). When the ultrasound transducer, which is typically cylindrical, emits the ultrasonic waves in radial directions into the fluid-filled balloon, the waves are reflected and redirected (focused) forward by the common reflective interface wall between the two balloons, and re-directed forward of the balloons and focused to define, for example, a focused ring-like ablation region in the circumferential interior OS annular wall. Such radial or circumferential ablating devices provide an efficient and effective means by which to simultaneously circumferentially ablate myocardial tissue around the OS of the pulmonary vein. Typically, multiple pulmonary ostia are ablated separately and sequentially with the same device as it is moved and placed in each OS needing ablation.

However, these known devices are not without their drawbacks. For instance, one function of the balloons of the ablating device, when the ablation element is inserted within an orifice or OS and inflated, is to serve as a blood flow barrier to seal the interface between the balloons and the inner annular wall of the orifice or OS, thereby temporarily preventing blood flow past the balloons through the OS. If the blood flow is not stopped substantially completely around all 360 degrees, then the residual blood flow may prevent thermal lesioning due to unwanted cooling of target tissues. However, when the balloons are manufactured and then inflated, they are manufactured and inflated to be rotationally symmetric (bodies of revolution) because it is the most manufacturable approach and does not require any rotational device alignment to target tissues. Conversely, the orifices or ostia within which the device, and the ablation element thereof, in particular, is to be inserted are not typically rotationally symmetric, but rather oftentimes are irregular and have a more oval or oblong shape with, for example, as much as a 3:1 aspect ratio. As such, when the balloons are inflated in an oval-shaped or irregular orifice, a sealed (to blood flow) interface between the balloon(s) and OS cannot be created, and as a result, cooling blood may leak past the balloons across the interface where ablative heating is to take place. When the blood leaks past the balloon(s), it undesirably serves to cool the surface of the tissue over which it flows, and does so in a non-uniform manner that cannot be easily corrected or compensated for. This is undesirable as these unintended cooled areas of tissue cannot be sufficiently continuously ablated or burned because they are being cooled by the blood, therefore, surface lesions cannot be controllably formed. Accordingly, the quality and adequacy of the ablation procedure may be substantially reduced, or require additional ablating procedures to be performed in order to complete the desired continuous ablation lesion of the targeted tissue.

Another drawback in known endocardial catheter pulmonary vein ostia ablation systems relates to the monitoring, maintenance, and/or control of the temperature in non-targeted tissue proximate the targeted ablation site during the ablation procedure. Such non-targeted tissue must not be damaged during the ablation procedure. More particularly, when certain heart tissue is being ablated, the energy emitted from the ablating device may be strong enough or generate a high enough temperature to cause tissue necrosis in non-targeted tissue. For example, portions of the esophagus are located proximate the heart and if an endocardial ablation site is near the esophagus the ablation energy itself, or heat generated by it and conducted away from the target, can potentially cause the nearby esophageal tissue to experience cell death.

Conventional suggested methods of addressing this concern include the use of one or more thermocouples or thermistor-based sensors that are passed either blindly or with the assistance of imaging or visualization systems (e.g., fluoroscopic, impedance-based, MRI, etc.) down the throat on an expandable member configured to monitor the temperature of the esophageal tissue and detect undesirable energy transfer to the esophagus. Such a technique may require the use of a dense macroscopic thermistor array, which may result in a disposable temperature monitoring device being cost-prohibitive or large. Additionally, such a technique may cause challenges with respect to the accuracy of the placement of the sensor(s), and it may be difficult to detect loss-of-contact between the sensor and the non-targeted tissue to be protected, or to sense the actual positioning of the sensor relative to the non-targeted tissue. Further, without using one or more imaging means, it is exceedingly difficult to locate a single protective thermocouple directly opposite or in the field of energy delivery of the ablating device. If such difficulty is compensated for by providing a thermocouple or thermistor array of larger area, another issue is presented, that being obtaining good thermal contact to the esophageal interior. Finally, apparent proper placement of the monitoring thermocouple using fluoroscopy still cannot guarantee proper thermal contact to the esophagus, or thermal wetted contact to the esophagus (i.e., a wet contact which stays wet and thermally sinking during an ablation procedure so as prevent the corresponding tissue from drying out and overheating).

Accordingly, there is a need for an ablation tool or system that will minimize and/or eliminate one or more of the above-identified deficiencies.

BRIEF SUMMARY OF THE INVENTION

The present disclosure is directed to an ablation system and its constituent components that include blood leakage minimization and tissue protective capabilities during an ablation procedure. The system according to the present teachings includes an ablating device configured to be inserted into the anatomy of a patient and to deliver ablating energy to a target-tissue ablation site. The system further includes a protective probe. The protective probe is configured for insertion into the anatomy of a patient and to be positioned in close proximity to a region of non-targeted tissue proximate the ablation site such as on the opposite side of the region of non-targeted tissue from the ablating device or collateral to the targeted ablation site.

In one exemplary embodiment, the ablating device comprises an elongate shaft having a proximal end and a distal end. The ablating device further includes a handle mounted to the elongate shaft at the proximal end thereof. The ablating device still further includes an ablation element mounted to the elongate shaft at the distal end. The ablation element includes an ultrasound transducer and at least one inflatable balloon surrounding the ultrasound transducer. The balloon includes an inner surface and an outer surface, and has a layer of shape-conforming gel disposed on at least a portion of the outer surface.

In one exemplary embodiment, the probe includes an elongate shaft having proximal and distal ends, and a longitudinal axis extending from the proximal end to the distal end of the shaft. The probe further includes a handle disposed at the proximal end of the shaft, and a tissue protecting apparatus disposed at the distal end of the shaft. The tissue protecting apparatus extends from a point on the shaft at or near the distal end thereof a predetermined distance along the longitudinal axis of the shaft toward the proximal end of the shaft. The tissue protecting apparatus is configured to protect non-targeted tissue in the region of non-targeted tissue from receiving unintended ablation energy intentionally targeted at nearby opposed, collateral, or upbeam targeted tissue, such as, for example, ablation energy delivered to tissue opposite the region of non-targeted tissue from the tissue protecting apparatus.

In accordance with another aspect of the present disclosure, an apparatus for use in monitoring temperature in a region of non-targeted tissue during an ablation procedure performed on targeted tissue proximate the region of non-targeted tissue is provided. The apparatus includes a probe configured to be inserted into the anatomy of a patient, and includes a proximal end and distal end. The apparatus further comprises a temperature monitoring apparatus associated with the probe, at least a portion of which is disposed at or near the distal end thereof. The temperature monitoring apparatus has a field of view and is configured to generate an image of the tissue disposed within the field of view, and to detect temperatures in the imaged tissue.

In accordance with yet another aspect of the present disclosure, a method of monitoring temperature in a region of non-targeted tissue during an ablation procedure performed on targeted tissue proximate the region of non-targeted tissue is provided. The method comprises a first step of providing a protective probe including a temperature monitoring apparatus having a field of view, wherein the probe and at least a portion of the temperature monitoring apparatus is configured to be inserted into the anatomy of a patient. The method includes a second step of thermally or thermographically imaging tissue within the field of view of the temperature monitoring apparatus and disposed within the non-targeted region of tissue. The method includes a third step of detecting at least one temperature of the imaged tissue, which, in an exemplary embodiment, is the maximum temperature in the imaged tissue.

The foregoing and other aspects, features, details, utilities, and advantages of the present teachings will be apparent from reading the following description and claims, and from reviewing the accompanying drawings.

DETAILED DESCRIPTION OF THE INVENTION

Figure 1:
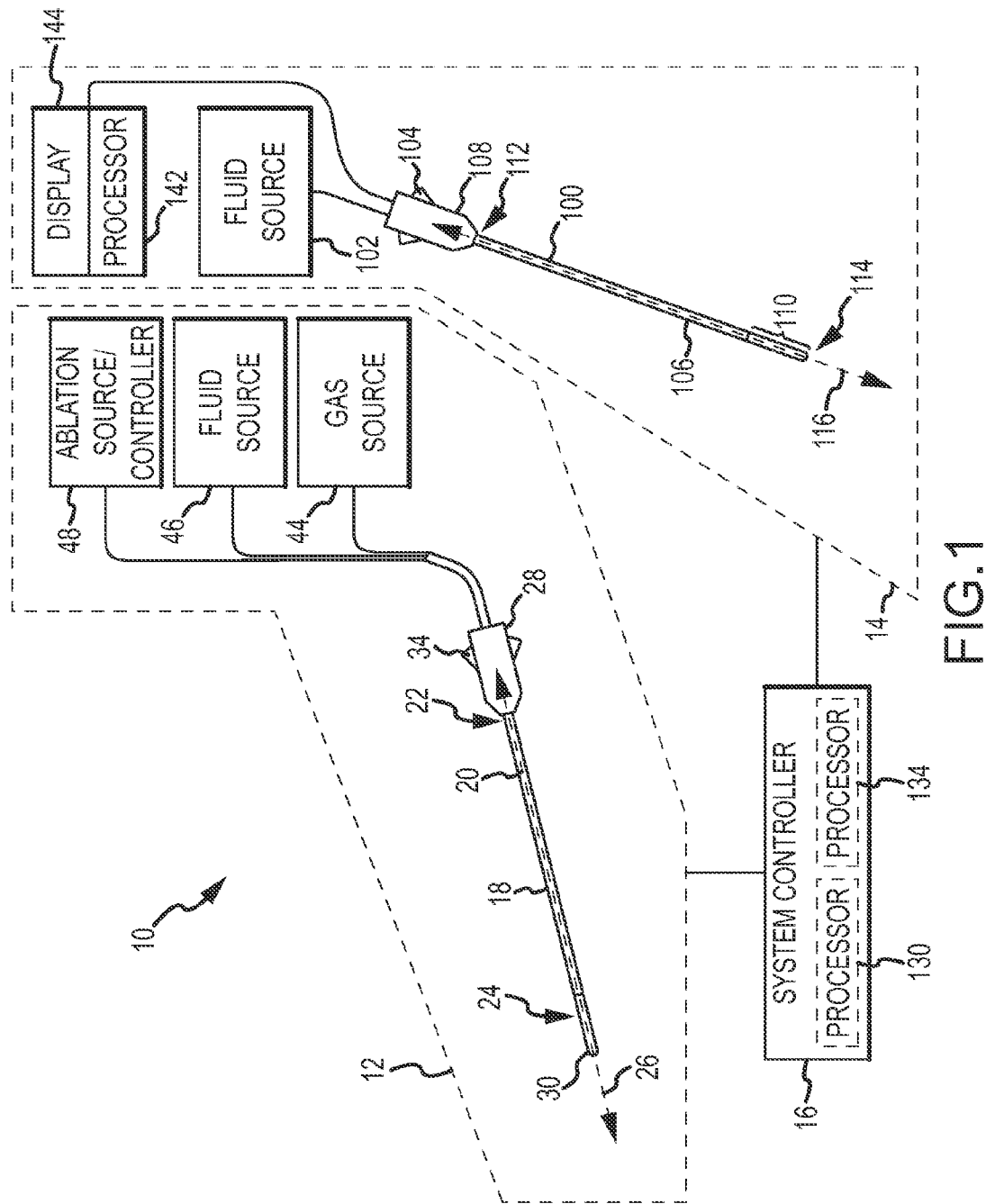
FIG. 1 illustrates a diagrammatic view of an exemplary embodiment of a system for performing an ablation procedure, and for monitoring and/or managing the temperature generated proximate an ablation site during the ablation procedure, in accordance with the present teachings.

Referring now to the drawings wherein like reference numerals are used to identify identical components in the various views, FIG. 1 illustrates an exemplary embodiment of a system 10 for performing ablation procedures and for monitoring, managing, and/or controlling the temperature in non-targeted tissue proximate an ablation site during the ablation procedure, in accordance with the present disclosure. The system 10 includes an ablation subsystem 12, a temperature monitoring and management subsystem 14, and, in an exemplary embodiment, a system controller 16 connected to each of the ablation subsystem 12 and the temperature monitoring and management subsystem 14. As is generally known in the art, (see, for example, U.S. Pat. No. 6,635,054 entitled "Thermal Treatment Methods and Apparatus with Focused Energy Application," U.S. Patent Publication No. 2004/0176757 entitled "Cardiac Ablation Devices," and International Publication No. WO 2005/102199 entitled "Ablation Devices with Sensor Structures", the disclosures of which are hereby incorporated by reference in their entireties), in an exemplary embodiment, the ablation subsystem 12 includes an ablating device 18, comprised, in part, of at least one ablation element 30 coupled to an elongate and typically flexible shaft 20 having a proximal end 22, a distal end 24, and a longitudinal axis 26 extending from the proximal end 22 through the distal end 24. As will be described in greater detail below, the ablating device 18 further includes a handle 28 coupled to the elongate shaft 20 at the proximal end 22 thereof, and the at least one ablation element 30 is mounted to the elongate shaft 20 at or near the distal end 24 thereof. While it should be understood that the ablating device 18 may include one or more ablation elements 30, and that ablating devices 18 having more than one ablation elements 30 are within the spirit and scope of the present disclosure, for ease of description purposes only the description below will be limited to an embodiment wherein the ablating device 18 includes a single ablation element 30.

The flexible elongate shaft 20 may be formed of any number of materials, such as, for example and without limitation, PEBAX®, Nylon, and polyurethane. In another exemplary embodiment, the elongate shaft 20 is constructed of, or incorporates, a metal wire braid, as is known in the art. The elongate shaft 20 further includes at least one, and typically multiple, inner passageways or lumens 32 disposed therein (shown in FIG. 2). The lumens 32 extend longitudinally along an axial portion of the shaft 20 from the proximal end 22 to the distal end 24, and are configured to have one or more components of the ablating device 18 disposed therein, such as, for example and without limitation, pull wires, planarity wires, fluid irrigation or drainage lumens, lead wires for the ablation element 30, a rotation wire, or, as will be described in greater detail below, components required for inflating and deflating balloons with, for example, fluid, gas, and/or extruding gels, associated with the ablating device 18, and the ablation element 30, in particular.

As briefly described above, the handle 28 of the ablating device 18 is disposed at the proximal end 22 of the elongate shaft 20. The handle 28 is operative to, among other things, effect movement of the shaft 20 (i.e., steer the ablating device 18), and/or selectively manipulate the distal end 24 of the elongate shaft 20 to position the distal end 24, and therefore, the at least one ablation element 30, in a desired location when the ablating device 18 is disposed within a patient. More particularly, in one embodiment provided for exemplary purposes only, one or more pull wire(s) (not shown) are coupled to and between both the distal end 24 of the elongate shaft 20 and an actuator(s) 34 located on the handle 28. As the actuator 34 is manipulated, the corresponding pull wire(s) is caused to be pushed and pulled, for example, to effect movement, such as bending deflection, of the distal end 24 of the elongate shaft 20. It should be noted, however, that while only this particular method or technique of steering or effecting movement of the elongate shaft 20, and/or the distal end 24 thereof, is described in detail herein, the present invention is not meant to be so limited. Rather, those of ordinary skill in the art will appreciate that other methodologies or techniques of steering and/or manipulating ablating devices exist that remain within the spirit and scope of the present invention. In addition to actuator 34, other components may also be disposed within the handle 28. For example, electrical matching circuits to electrically impedance-match the components of the ablation element 30 to an ablation energy generator or power source, or other components of the ablation subsystem 12, for example, may be disposed within the handle 28. The ablation element 30 and the energy generator can be configured to deliver one or more types of ablation energy (e.g., high intensity focused ultrasound, or HIFU, radiofrequency, laser, microwave and the like).

Figure 2:
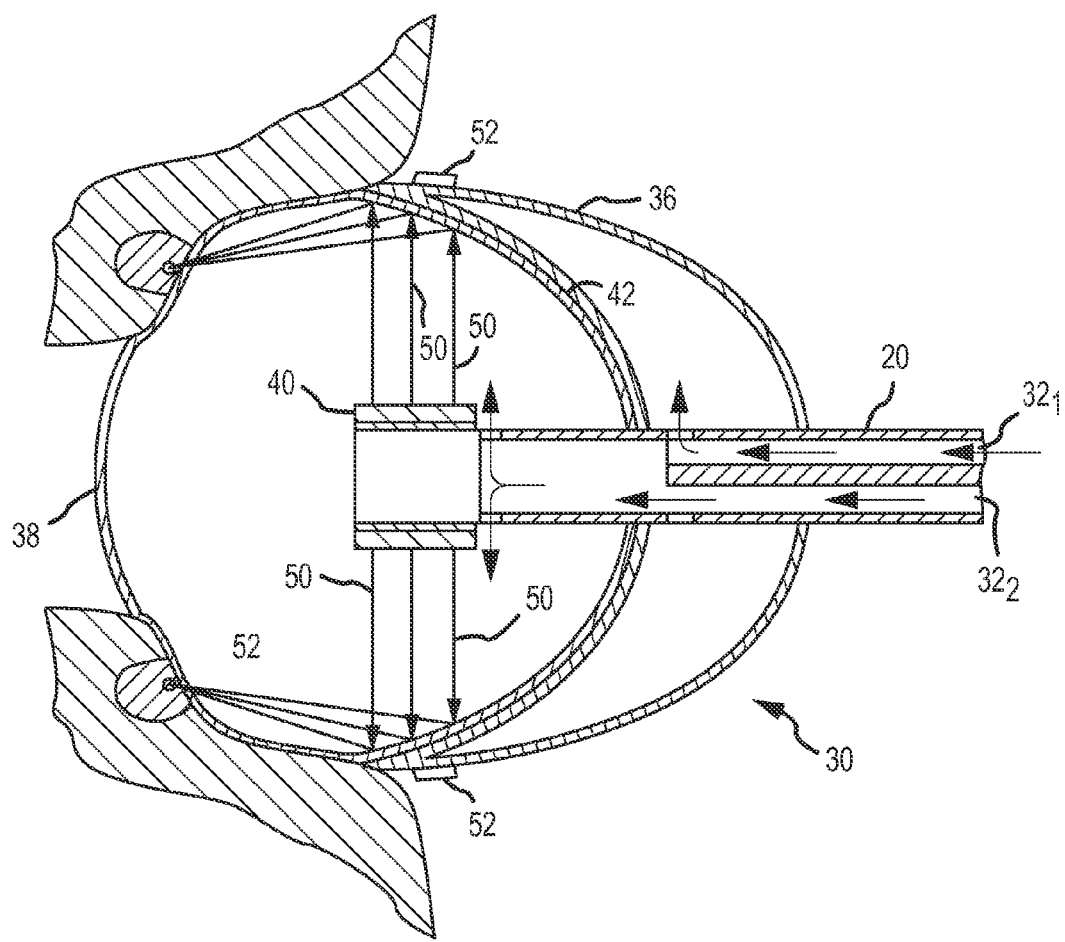
FIG. 2 is a partial cross-section view of an exemplary embodiment of an ablation element of an ablating device of the system illustrated in FIG. 1, wherein balloons of the ablating device are inflated.

With reference to FIG. 2, the ablation element 30 of the ablating device 18 will now be described. In an exemplary embodiment wherein the ablation element 30 is configured to deliver ultrasound energy to target tissue, the ablation element 30 includes a pair of inflatable balloons 36,38, and an ultrasound transducer or emitter 40 (hereinafter "ultrasound transducer 40" or "transducer 40") mounted within one of the balloons (i.e., the distally disposed fluid-filled balloon 38, for example). In an exemplary embodiment, the transducer 40 may take the form of tubular or cylindrically-shaped ultrasound transducer formed of a piezoelectric material (e.g., piezoceramic, for example) which radiates ultrasound in radial directions around all 360 degrees. If, as will be described below, the transducer 40 is rotatable about the axis 26 during ablation, it may comprise a full cylinder or an angular sector of a cylinder. When the balloons 36,38 are deflated or in a collapsed condition, they form a small and compact unit that is substantially flush with the outer surface of the elongate shaft 20, or at least forming a low profile therewith, so as to allow the ablating device 18 to be easily inserted into and removed from a patient's body. Alternatively, the ablating device 18 may be inserted into and removed from a patient's body via a sheath or introducer (not shown).

As illustrated in FIG. 2, when in an inflated state, the balloon 38 is positioned distally or forward relative to the balloon 36. The two balloons 36,38 share an acoustically reflective common wall or balloon-wall interface 42 that, in the inflated state, essentially forms a parabolic surface with, as will be described below, fluid on one side and gas on the other side. In an exemplary embodiment, the common wall 42 comprises a single layer of material such that the wall is integral with each balloon 36,38 and therefore is truly shared by the balloons 36,38. In another exemplary embodiment, such as that illustrated in FIG. 2, the wall 42 comprises two layers of material that are fused or otherwise joined together to form a single wall (i.e., each balloon 36,38 has a wall, and the walls are fused or joined together to form a single wall). In yet still another embodiment, the common wall 42 is formed by the respective walls of the balloons 36,38 abutting each other to form a single wall.

As will be described in greater detail below, in an exemplary embodiment, the balloon 38 is inflated with an acoustically-transmissive fluid or flowable material, such as, for example, liquid saline or gel, while the balloon 36 is inflated with a gas, such as, for example, biocompatible carbon dioxide ($CO_2$). Accordingly, when the balloons are in an inflated state, the common wall 42 has saline on one side (i.e., inside balloon 38) and gas on the other side (i.e., inside balloon 36). As such, the fluid/gas interface acts as an acoustic mirror, and so by shaping the common wall 42 as, for example, a parabola, the ultrasound waves emitted from the transducer 40 are reflected and focused (reflectively focused) into an annular lesion target region in the wall of the OS (the target tissue), as is illustrated in FIG. 2.

Accordingly, in operation, a practitioner inserts the distal portion 24 of the elongate shaft 20, and therefore, the ablation element 30 with its balloons deflated or in a collapsed condition, into an incision in a patient's body, for example. The practitioner may then advance the device through the patient's vasculature until it reaches a desired location (e.g., an ablation site within the heart, such as, for example, an orifice or OS connecting a pulmonary vein with the left atrial chamber of the heart). The desired location may be within the OS, or, alternatively, may be a location external to the OS. Once the desired location is reached, the balloons are inflated, as will be described in greater detail below, and the ablation procedure can be carried out. In the instance where the desired location is external to the OS, the balloons 36,38 may be inflated and then advanced into the OS, rather than being inflated within the OS.

In an exemplary embodiment, the gas-filled balloon 36 is coupled with, and configured to be inflated by, a gas source 44 (shown in FIG. 1). More particularly, one of the lumens 32 disposed within the elongate shaft 20 is configured to be an inflation lumen (hereinafter "lumen 32$_1$") and is further configured to couple the balloon 36 to the gas source 44 that supplies gas, such as, for example, carbon dioxide, under pressure to the balloon 36. Accordingly, when the gas source 44 is activated, the balloon 36 inflates. Typically, a controlled gas pressure will be maintained in the balloon 36 to maintain a controlled balloon firmness.

Conversely, in an exemplary embodiment, the fluid-filled balloon 38 is coupled with, and configured to be inflated by, a fluid or liquid source 46 (shown in FIG. 1). More particularly, one of the lumens 32 disposed within the elongate shaft 20 other than the inflation lumen 32$_1$ associated with the balloon 36 is configured to be an inflation lumen (hereinafter "lumen 32$_2$") and is further configured to couple the balloon 38 to the fluid source 46 that supplies fluid, such as, for example, isotonic saline solution, to the balloon 38. Accordingly, when the liquid source 46 is activated, the balloon 38 inflates. As with the gas in the balloon 36, the fluid in the balloon 38 will typically be pressurized to a desired level to maintain a controlled balloon firmness. The gas and fluid pressurization levels, although not necessarily equal in magnitude, are chosen to assure full distended inflation of the balloons 36,38 yet be below the burst pressures of the respective balloons.

Additionally, when the balloons 36,38 each transition from an inflated to a deflated states, the gas and fluid in the respective balloons 36,38 must be drained or otherwise removed or expelled from the balloons 36,38. In an exemplary embodiment, the lumens 32 through which the gas and fluid were delivered to the balloons 36,38 also serve the purpose of providing a path through which the gas and the fluid in the balloons 36,38 is returned to the respective gas/fluid sources 44,46, or otherwise drained or expelled. In such an instance, the respective lumens 32 may be selectively coupled with a suction source, vent, or drain to cause or allow the gas/fluid in the balloons 36,38 to exit the balloons 36,38. Alternatively, separate drainage lumens (not shown) may be provided within the elongate shaft 20 to carry out the above described functionality.

As can be seen in FIG. 2, and as was described above, the gas-filled balloon 36 and the fluid-filled balloon 38 share the common wall 42. As was also briefly described above, when the balloons 36,38 are inflated, the common wall 42 acts as an acoustic reflecting and focusing mirror capable of reflecting ultrasonic waves emitted by the transducer 40. It is primarily the fluid/gas acoustic impedance discontinuity that provides this efficient acoustic reflection capability and the thin balloon wall 42 physically maintains the fluid/gas interface. However, while the fluid/gas interface substantially provides the acoustically reflective capability, it should be understood that both the material of the balloon and its thickness do have a small, but nonzero, effect on reflectivity, particularly when it is thin as inflated.

With continued reference to FIG. 2, in an exemplary embodiment, the ultrasound transducer 40 is mounted to the distal portion of the elongate shaft 20 at or near distal end 24 thereof, for example, and within the balloon 38. It should be noted, however that in other exemplary embodiments that remain within the spirit and scope of the present invention, the transducer 40 may be mounted to structure within the balloon 38 other than the elongate shaft 20. Additionally, the transducer 40 may be positioned within the balloon 38 at a number of locations, including, for example, at the back (proximal region) of the balloon 38 close to or abutting the common wall 42.

In an exemplary embodiment wherein the ultrasound transducer 40 comprises a tubular cylindrical emitter and the balloons 36,38 are in an inflated state, the ultrasound transducer 40 uniformly emits acoustical energy from its cylindrical outer surfaces around the 360 degrees of that outer surface directed toward the shaped mirror fluid/gas interface (i.e., common wall 42). It will be appreciated by those having ordinary skill in the art that the transducer 40 may be driven in a lower frequency "breathing" mode, or in a higher frequency "wall thickness" mode, and/or in harmonics of these. The transducer 40 may further include overlying matching layers (not shown) or interior back materials (not shown). The transducer 40 may further be "pinged" such that, using the pulse-echo approach, the lesion and/or thickness or depths thereof may be assessed.

As illustrated in FIG. 1, the transducer 40 is electrically connected to an energy or ablation power source 48 by electrical leads or wires (not shown) that are disposed within one or more of the lumens 32 in the elongate shaft 20, and that extend through to the proximal end 22 thereof. When the ablation power source 48 is activated, the transducer 40 emits ultrasonic waves 50 along various paths in radial direction relative to the longitudinal axis 26 (i.e., toward the common wall 42 between and defined by the balloons 36,38). As shown in FIG. 2, and as briefly described above, as the acoustic waves 50 impinge upon the reflective fluid/gas interface (i.e., the common wall 42), they are reflected as illustrated in FIG. 2 and simultaneously focused into a ring-like ablation region. The focused ablation region permits the efficient and effective ablation of targeted myocardial tissue, for example. It should be noted that, as is generally known in the art, the transducer 40 may be omnidirectional and/or rotatable relative to the balloons 36,38 about the axis 26. Rotation allows for circumferentially uniform energy exposure (lesioning extent) despite having some circumferential non-uniformity of the circumferential output of the transducer 40. Accordingly, by rotating the transducer 40, any angular non-uniformity of acoustic output will be rotated such that all tissue target points on the OS receive the integrated same time-power treatment. Therefore, rotating the transducer 40 allows use of a less-uniform transducer. Alternatively, using rotation, other transducers, such as, for example, a directional transducer (emitting less than 360 degrees at a given moment), whether cylindrical or not, may be used. In an embodiment wherein the transducer 40 is rotated, a rotation wire (not shown) coupled with the transducer 40 and manually driven from a control on the handle 28, or driven by a motor, may be employed to cause the transducer to rotate.

In addition to serving to cooperatively form the reflectively focusing surface for the ultrasonic waves emitted by the transducer 40, one or both of the balloons 36,38 are configured and operative to serve other purposes. More particularly, when inserted into an orifice or OS between a vein and the heart, for example, and inflated (or inserted already inflated), the balloons 36,38 are intended to serve as a barrier to blood flow through the orifice or OS, and/or to generally center the transducer 40 in the OS. However, one disadvantage with known ablating devices is that when inflated, the balloons of the device are rotationally symmetric. However, most orifices or ostia into which the device is inserted are not rotationally symmetric, but rather are irregular and/or have an oval or other similar non-round shape. Accordingly, when the device is inserted into the oval-shaped orifice and the rotationally symmetric balloons are inflated, a sealed blood flow between the balloons and the adjacent surface of the orifice or OS cannot be achieved, or at least cannot be achieved without potentially damaging force being applied to the OS. Because the interface is not sufficiently sealed, blood may be permitted to leak through any balloon-OS gaps, which may act to cool the local surface of the orifice or OS that is being ablated. When the tissue is cooled by the blood flow, it counteracts the ablation procedure, thereby preventing surface and/or somewhat deeper lesioning. Therefore, one aspect of the present invention is directed to the elimination, or at least the substantial reduction, of blood leakage cooling experienced in these ablating devices.

Accordingly, with reference to FIG. 2, one exemplary embodiment of the ablating device 18 with blood leakage minimization capability operative to eliminate, or at least substantially prohibit, blood flow leakage past the balloon(s) 36,38 in the balloon/OS interface is illustrated. In this exemplary embodiment, at least a portion of the outer surface of one or both of the balloons 36,38 is coated with a gel 52, such as, for example, a low-flow or pressure formable gel, which acts as a conformable or deformable gasket material to stop blood flow in non-round ostia. The gel 52 may comprise one of many different known types of biocompatible implantable gels. One gel, provided for exemplary purposes only, is that available from MacroMed, Inc. under the trademark ReGel®. Another exemplary gel that may be used is that available from Mebiol, Inc. under the name "Mebiol Gel." The latter exemplary gel hardens upon exposure to a sufficient amount of heat, and softens upon subsequent cooling. The gel can be fabricated of a biocompatible and bio-absorbable material as well. It will be appreciated by those of ordinary skill in the art that any number of gels could be used, and thus, the invention is not limited to those specifically identified above. In an exemplary embodiment, the gel is acoustically transparent and so it will not block or substantially impede ablative energy emitted by the ablating device, such as, for example, high-intensity focused ultrasound (HIFU) ablating devices. Additionally, in an exemplary embodiment, the gel is of a type such that it will not boil or bubble below about 100° C. Those having ordinary skill in the art will appreciate that while gels are typically network polymers which are water or solvent based, the term "gel" as used in accordance with the present disclosure is intended to include any material whose flow resistance can prevent it from being displaced or washed way by blood pressure and blood flow. Therefore, the gel may be prepositioned on the outer surface of one or both of the balloons 36,38, or might be extruded from the balloon, but in any event, will have a viscosity high enough that it resists the blood flow forces while allowing for physical conformance to non-round OS geometries.

As illustrated in FIG. 2, in one exemplary embodiment, it is the outer surface of the balloon 36 that has the gel 52 disposed thereon. In other exemplary embodiments, however, in addition to or instead of the gel 52 being disposed on the outer surface of the balloon 36, the gel 52 is disposed on the outer surface of the balloon 38, or at the interface between the two balloons 36,38. The gel 52 is configured to act as a blood flow-seal between the balloon(s) 36,38 and the interior surface of an orifice or OS into which the ablating device 18 is inserted. In other words, the gel 52 fills gaps between the outer surfaces of the balloons 36,38 and the interior and/or face surfaces of the orifice or OS to inhibit blood flow therebetween. Once the gaps are filled, the gel 52 may or may not further stiffen (i.e., upon exposure to heat or cooling), however, in an exemplary embodiment, the gel has a fixed viscosity sufficient to conform yet still block blood flow.

In an exemplary embodiment, at least a portion of the outer surface of one or both of the balloons 36,38 is coated with a layer of the gel 52 prior to the ablating device 18, and the distal portion of the elongate shaft 20, in particular, being inserted into a patient's body. In such an embodiment, when the balloons 36,38 are inflated, the gel 52 is already disposed on either the entire outer surface of the balloon(s) 36,38, or a portion(s) thereof. In an alternative embodiment, rather than pre-coating the surface of the balloon(s) 36,38 with the gel 52, the ostia or OS are pre-coated with the gel. In such an embodiment, a separate gel application tool (possibly including a gel extruding permeable balloon) may be used to coat the OS. In another exemplary embodiment, the ablating device 18 itself may have the capability to apply the gel to the surface of the OS as by pressurized extrusion out of one or more orifices.

In another exemplary embodiment wherein the balloon(s) 36,38 are coated with the gel 52, the ablating device 18 is configured such that the gel 52 is distributed onto at least a portion of the outer surface of the balloon(s) 36,38 after the balloon(s) are inflated rather than prior to insertion into the patient's body. In an exemplary embodiment, rather than the balloon 38 being inflated with a liquid such as saline, the balloon 38 may be inflated with a gel. In such an embodiment, the balloon 38 is configured and constructed of a gel-permeable material to ooze or leak the gel therefrom and into the balloon/OS interface gaps. Alternatively, the balloon may include one or more perforations or outlets (not shown) therein to allow gel in the balloon to flow out of the balloon when a modest amount of pressure is applied to the gel (when the pressure is removed, the gel stops flowing). Such gel gasket extrusion may take place as part of the balloon inflation process. Accordingly, in this embodiment the gel would serve not only the blood leakage minimization function, but to also act with the gas used to inflate the balloon 36 as the fluid/gas mirror. One exemplary type of gel that is suitable to serve this dual function is a sufficiently acoustically transparent water-based gel. In another exemplary embodiment wherein the common wall 42 comprises the walls of each of the balloons 36,38 abutting each other to form a single wall (as opposed to a single layer or two fused layers), a dedicated gel distribution lumen (not shown) may deliver gel to the interstitial space between the two balloons 36,38 through a port (not shown) within the shaft 20. As a result of capillary action, the gel will be pushed out to the periphery, and therefore, onto the surface(s) of the balloon(s) 36,38.

The gel 52 may be held in or on the balloon(s)/OS interface in a number of ways. In an exemplary embodiment, the gel 52 is configured to solidify or stiffen when sufficiently heated. The gel 52 may be heated in any number of ways, such as, for example and without limitation, by the heat generated by the ablation procedure being performed proximate to the location of the gel 52, by the gel 52 being exposed to body temperature of the patient, or by separate and distinct heat source. For example, and without limitation, heated saline maybe delivered to or circulated within the balloon 38, a resistive wire may be disposed within the balloon 38, a heated gas may be delivered to or circulated within the balloon 36, and the like. It will be appreciated that the particular temperature required to stiffen the gel will be dependent upon the gel used, however, an exemplary temperature may be, for example and without limitation, 39° C., which is slightly higher than body temperature. For illustrative, not limiting, purposes, in an embodiment wherein a gel such as ReGel® described above is used, the relative amounts of the two constituent type A and B block copolymers may set such that the gel stiffens at a particular desired temperature.

In another exemplary embodiment, rather than solidifying or stiffening when exposed to heat, the gel 52 solidifies or stiffens when sufficiently cooled. In such an embodiment, any means by which the gel may be cooled may be used, such as, for example and without limitation, an artificial cooling means. In such embodiment, the ablation element 18 may include a cooling or heat-extracting device (not shown) configured to sufficiently cool the gel 52 to cause it to solidify or stiffen. For example, and without limitation, cooled saline or some other cryogenic or cold fluid may be delivered to or circulated within the balloon 38, a cooled gas may be delivered to or circulated within the balloon 36, and the like.

Notwithstanding the description above, it will be appreciated by those having ordinary skill in the art that any number of biocompatible gels which will not substantially flow during an ablation procedure under modest blood flow pressure (i.e., the gel is thick and viscous or thixotropic enough to physically maintain its position and form during the ablation procedure) may be used for the purposes described above. In any instance, depending on the particular gel used, the gel may be left in the patient's body for immediate or gradual dissolution or biodegradation after the ablation procedure is completed. One way to leave the gel within the body is to leave it on the OS interior in "molded" form for gradual surface-wise dissolution. Alternatively, using temperature manipulation (by removing heat, and/or otherwise heating or cooling the gel), the gel may be reflowed or re-liquefied after the completion of the ablation procedure to ensure that no solid or semi-solid lumps of gel are left in the circulatory system for any period of time.

In addition to, and independent of, the blood leakage concerns described above, another drawback to known ablating devices is that it oftentimes proves difficult to reliably monitor temperature and/or sufficiently cool non-targeted regions of tissue proximate an ablation site during the performance of an ablation procedure. One such non-targeted region of tissue, which is provided for exemplary and illustrative purposes only, is esophageal tissue disposed close to the heart. More particularly, as ablating energy is directed to a region of the heart by an ablating device, such as, for example and without limitation, any endocardially-delivered ablating device including radio frequency (RF), microwave, cryogenic, and ultrasound-based devices, the ablating energy may have sufficient strength and intensity to pass through and outward of the heart and be applied to non-targeted tissue in the esophagus that is located on the other side of the ablated tissue from the ablating device. Likewise, even if the ablating energy itself does not directly penetrate that far, if a large hotspot is developed at the target site, then the non-targeted tissue may be overheated simply due to proximity. In either instance, this may cause the temperature in the esophageal tissue to rise, thereby forming "hotspots" that may potentially cause cell death within or on the esophagus. The burning of this tissue may cause severe damage to the esophagus. Therefore, another aspect of the present invention is directed to the improved monitoring, management, and/or control of temperature rise or energy delivery in non-targeted tissue regions proximate an ablation site.

Accordingly, with reference to FIGS. 1 and 3-10, the temperature monitoring and management subsystem 14 of system 10 will now be described. In an exemplary embodiment, the temperature monitoring and management subsystem 14 includes a protective probe 100, a fluid source 102, and an actuator 104.

With continued reference to FIGS. 1 and 3-10, the probe 100 includes an elongate shaft 106, a handle 108, and a tissue protecting apparatus 110. As with the shaft 20 described above, the elongate shaft 106 has a proximal end 112, a distal end 114, and a longitudinal axis 116 extending from the proximal end 112 through the distal end 114. The handle 108 is disposed at the proximal end 112 and, as described above with respect to the handle 28, may be configured, among other things, to steer or manipulate portions of the probe 100 as it is inserted into the anatomy of a patient, such as, for example, the esophagus. In an exemplary embodiment, the probe 100 is directly inserted into the esophagus such as through the mouth or sinus. However, in another exemplary embodiment, the probe 100 is introduced into the esophagus through an introducer-lumen already in place. The tissue protecting apparatus 110 of the probe 100 is disposed at or near the distal end 114 of the elongate shaft 106.

In an exemplary embodiment, the tissue protecting apparatus 110 comprises a wetted heat sink (hereinafter "heat sink 110"). It should be noted that the term "heat sink" as used herein is intended to mean an element or structure having the capability of (i) carrying away heat deposited in the esophagus wall tissue by an OS ablator element(s) being used inside the heart of the patient, and/or (ii) cooling or pre-cooling the esophageal tissue that is to be protected. In either instance, this may be accomplished by either contacting the tissue or causing cooling fluid to be dispensed onto the tissue. The heat sink 110 is disposed at the distal end 114 of the elongate shaft 106 and extends therefrom a predetermined distance along the longitudinal axis 116 toward the proximal end 112 of the elongate shaft 106.

In one exemplary embodiment, the heat sink 110 comprises an inflatable balloon, membrane, or bladder 118 (collectively "bladder 118"). The bladder 118 has a collapsed or deflated condition, and an expanded or inflated condition. In the collapsed condition, the bladder 118 provides a low profile distal portion to probe 100, which is easily passed down the throat. In an exemplary embodiment, the bladder 118 is formed of an elastomeric material to assure that no folds occur upon inflation of the bladder 118. In another exemplary embodiment, the bladder may be pleated or folded upon itself when in the deflated condition, but configured to be inflated to a point ridding it of the folds or pleats at a diameter less than that of the esophagus such that when seated upon the esophagus during further inflation, not pleats or folds exist.

In an exemplary embodiment, the bladder 118 is configured to be inflated with a biocompatible fluid. However, in other exemplary embodiments the bladder 118 may be inflated with gas, air, gel, liquid or other suitable medium, including nutritious and/or therapeutic constituent elements or components. In the exemplary embodiment described hereinafter, the bladder 118 is inflated with liquid saline, but the present invention is not meant to be limited to saline. In addition to inflating the bladder 118, the fluid also serves as the coolant or heat transfer medium for either drawing heat away from, or for cooling or pre-cooling esophageal tissue. More particularly, and as will be described in greater detail below, the fluid (e.g., saline or another type of thermally conductive fluid, for example) may be kept inside and/or circulated within the bladder 118 such that heat in the tissue that the bladder 118 contacts (when, for example, the bladder 118 is inflated against esophageal tissue) is transferred to the fluid via thermal conducting through the thin bladder wall.

In addition, or alternatively, the bladder 118 may have perforations, microscopic holes, pores, outlets, permeation paths, and the like therein configured to allow the fluid in the bladder 118 to be leaked, weeped, sprayed, or otherwise dispensed therefrom upon the tissue to be protected in order to cool or pre-cool the tissue. In an exemplary embodiment, the fluid may be pre-cooled below body temperature such that esophageal tissue is actually sub-cooled below natural body temperatures.

Figure 3:
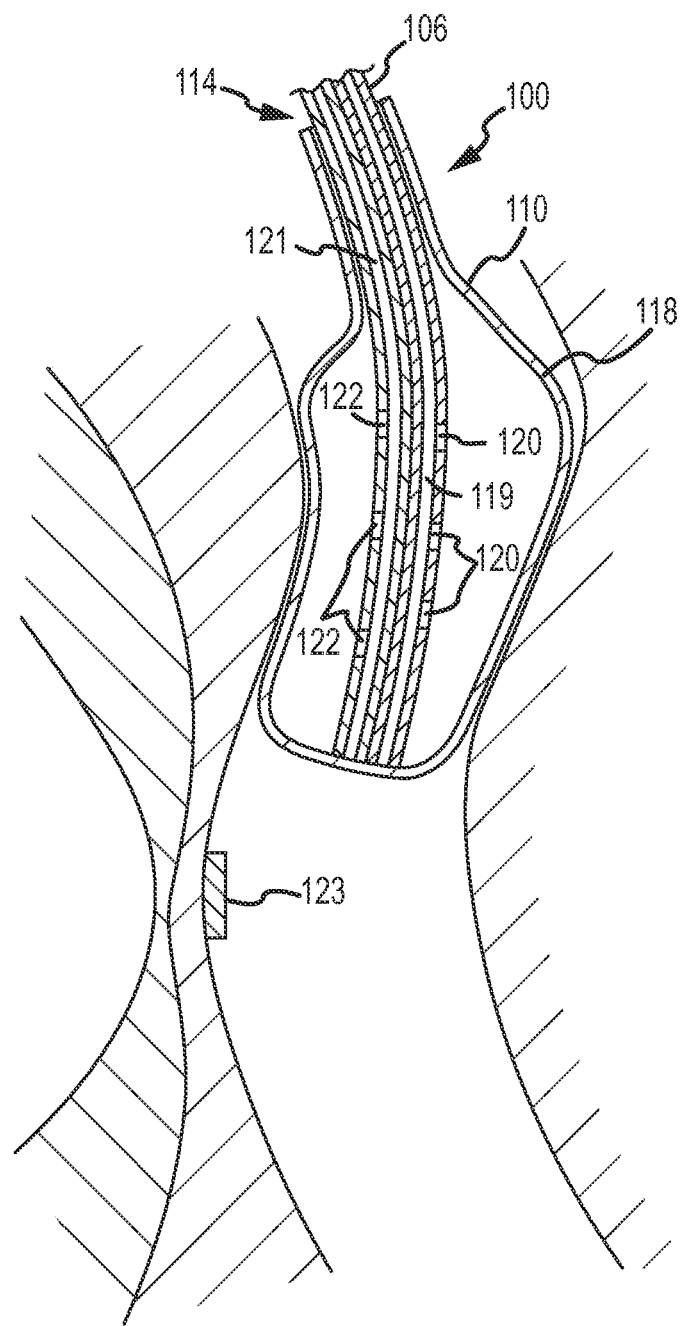
FIG. 3 is a partial cross-section diagrammatic view of an exemplary embodiment of a protective probe of a temperature monitoring and/or management subsystem of the system illustrated in FIG. 1, wherein the probe is disposed within the esophagus of a patient and includes a tissue protecting apparatus disposed at or near the distal end thereof.
Figure 4:
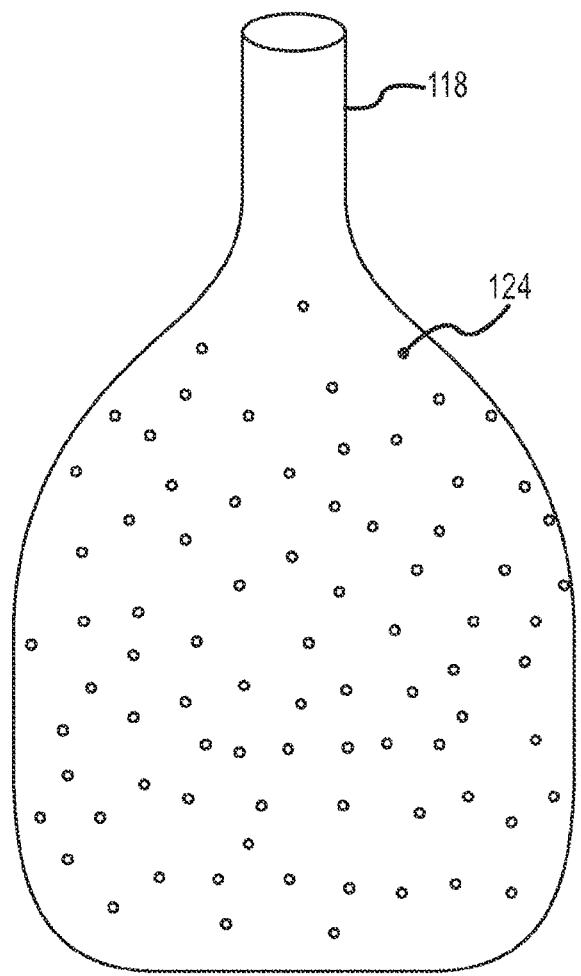
FIG. 4 is a schematic view of an exemplary embodiment of the tissue protecting apparatus illustrated in FIG. 3.
Figure 5:
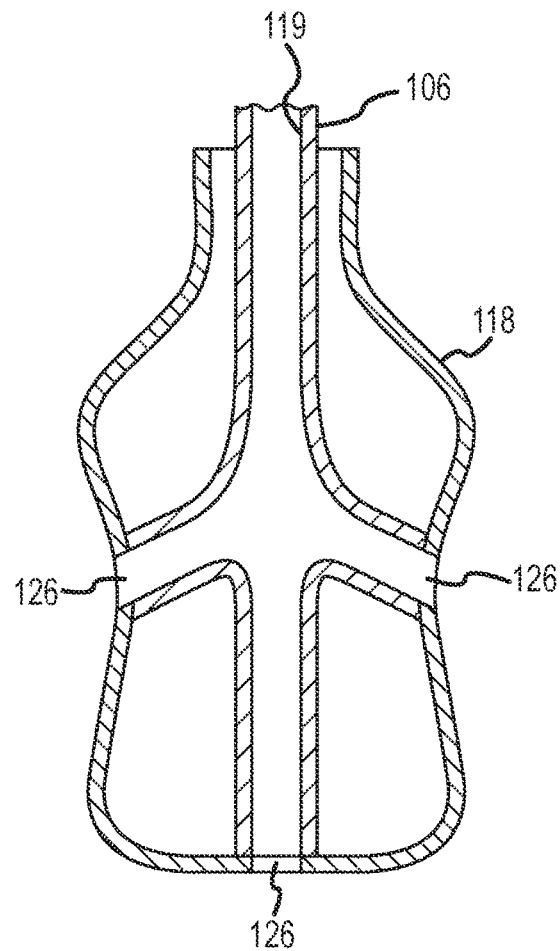
FIG. 5 is a cross-section view of an exemplary embodiment of the tissue protecting apparatus of FIG. 3 including fluid delivery lumens and corresponding outlets disposed therein.

Accordingly, in such an embodiment, the bladder 118 is connected to, or otherwise coupled with, an inflation or filling lumen 119 disposed within the elongate shaft 106 (shown in FIG. 3, for example). The inflation lumen 119 is disposed between, and coupled to, each of the bladder 118 and the fluid source 102 of the subsystem 14 to allow the bladder 118 to be inflated. In an exemplary embodiment, the fluid source 102 is configured to supply fluid, such as, for example, various saline solutions, distilled water, deionized water, or other forms of biocompatible water to the bladder 118. The fluid source 102 may include, for example, a reservoir containing a liquid and a pump, a gravitational feed arrangement, a syringe or other pumping device, or a tank containing fluid under pressure coupled to the inflation lumen 119 through a controllable pressure regulator. If water is to be ingested down the esophagus, a water composition similar to drinking water may be used (e.g., frozen, partially frozen, and/or at a reduced temperature) and may include flavorants or, as mentioned above, nutritious and/or therapeutic constituent elements or components that are delivered or circulated therethrough. Accordingly, as illustrated in FIGS. 3 and 6-8, the shaft 106 of the probe 100 includes one or more openings or ports 120 therein to allow fluid in the lumen 119 to flow into the bladder 118. In one exemplary embodiment, the distal end of the shaft 106 is open, thereby defining opening 120. In addition, or in the alternative, the shaft 106 may have one or more lateral openings or ports 120 in the wall thereof to allow fluid to flow into the bladder 118.

As briefly described above, in an exemplary embodiment, the subsystem 14 further includes the actuator 104, such as, for example and without limitation, a flow-volume controller, a pressure controller, or both. The actuator 104 is disposed between the inflation lumen 119 and the fluid source 102, and is configured to control the supply of fluid to the bladder 118, and therefore, the inflation of the bladder 118. In an exemplary embodiment, the actuator 104 is further configured to control the amount of fluid distributed from the bladder 118. The actuator 104 may be mounted on or otherwise associated with the handle 108 of the probe 100, or may be separate and distinct from the probe 100.

In an exemplary embodiment, the cooling fluid supplied to the bladder 118 by the fluid source 102 is circulated between the bladder 118 and the fluid source 102. More particularly, in an exemplary embodiment illustrated, for example, in FIG. 3, the probe 100 may further include a return or drainage lumen 121 (referred to hereinafter as "return lumen 121" and which may comprise lumen 119 or a separate and distinct lumen) disposed within the elongate shaft 106 to allow fluid to flow from the bladder 118 back to the fluid source 102 or to some other drain external to the patient. This allows, for example, fluid to be circulated through the system to facilitate the replacement of warmer fluid with cooler (i.e., pre-cooled) fluid, for example. In addition, it allows for much higher convective heat transfer from potential undesired esophageal-tissue hotspots.

In addition to aiding in the circulation (flow) of the fluid into the bladder 118, the return lumen 121 may also provide a means by which the bladder 118 may be emptied or deflated once the ablation procedure is concluded or the heat sink 110/bladder 118 is no longer needed (i.e., the actuator 104 may shut off the flow through the inflation lumen 119 and/or apply suction to the return lumen 121, thereby causing the fluid to be drained from the bladder 118 through the return lumen 121). Such a return lumen 121 could also be used in the same manner in an embodiment that does not include circulation of the fluid during use of the probe 100, but rather simply allows for the deflation of the bladder 118. In any event, the shaft 106 of the probe 100 includes one or more openings or ports 122 therein to allow fluid in the bladder 118 to flow into the lumen 121. In one exemplary embodiment, the distal end of the shaft 106 is open, thereby defining opening 122. In addition, or in the alternative, the shaft 106 may have one or more lateral openings or ports 122 in the wall thereof to allow fluid to flow into the lumen 121.

Accordingly, in operation, and in accordance with one exemplary embodiment, once the probe 100, and the distal portion thereof, in particular, is inserted and appropriately positioned within the patient's body (e.g., opposite the ablation element 30), the bladder 118 is inflated or filled so as to contact the inner surfaces of the passageway within which the probe 100 is inserted (e.g., the inner wall of the esophagus). The bladder 118 and the fluid therein is configured to spread and transfer the heat from the tissue to and through the surface of the bladder 118 and into the fluid in the bladder 118 to quell any hotspots (see reference numeral 123 in FIG. 3, for example) in the region of non-targeted tissue in contact with the probe 100.

In order to better distribute the heat from the non-targeted tissue about the surface of the bladder 118, and thus, better transfer the heat away from the tissue, in an exemplary embodiment the outer surface of the bladder 118 is coated with a thermally conductive material, such as, for example, a metallic thin-film material and/or a hydrophilic hydrogel.

In another exemplary embodiment, the bladder 118 comprises a thin-walled unmetallized (bare) balloon with internally circulating (or at least convecting locally) fluid. In such an embodiment, the wall of the bladder 118 is so thin (on the order of 15-40 microns, for example) that only a very small thermal gradient of a couple of degrees Celsius can be maintained across it. For example, in an exemplary embodiment provided for illustrative purposes only, the tissue cannot get any hotter than 2° C. above the bladder circulating fluid despite unintended ablation heating (presuming intimate wetted contact between the bladder 118 and the tissue). As has been or will be described elsewhere herein, in an exemplary embodiment, the exterior surface of the bladder 118 is hydrophilic or wettable such that the bladder/tissue interface is well-coupled thermally. A number of techniques may be used to ensure that the outer surface of the bladder 118 stays wetted. For example, and as will be described in greater detail below, the wall of the bladder 118 may include fluid-weeping or spray perforations or holes therein, or be fluid permeable, to assure its outer surface and surrounding tissue stay wetted. In addition, or alternatively, the outer surface of the bladder 118 may be gel coated to assure wetted contact between the tissue and bladder 118, and therefore, the heat sink 110. In an exemplary embodiment, the bladder 118 is configured to weep fluid therefrom in order to maintain saturation of the gel coating the surface of the bladder 118.

In an exemplary embodiment, the protective probe 100, and the heat sink 110 thereof, in particular, may be further configured to force-cool the tissue by flushing the tissue with fluid from the bladder 118 and/or from the fluid source 102. This force-cooling may be done prior to the commencement of an ablation procedure (i.e., pre-cooling the tissue), during the procedure, or a combination of the two. This may be accomplished in a number of ways. In one exemplary embodiment illustrated, for example, in FIG. 4, a plurality of perforations or holes 124 are formed in the wall of the bladder 118. The holes 124 permit the fluid within the bladder 118 to flow therefrom and onto the outer surface of the bladder 118 and/or the tissue proximate thereto. Obviously, the larger the holes, the more fluid will be dispensed from the bladder 118.

In another exemplary embodiment, the bladder 118 is configured to allow fluid to be sprayed therefrom and onto the surrounding tissue in an aerosol or steam-spray fashion. In this embodiment, the bladder 118 need not be designed to fit snugly against the esophageal wall and, in an exemplary embodiment, may be left hanging loosely in the esophagus. One means by which this may be done is to force air or gas into the bladder 118 causing the fluid in the bladder 118 to be dispensed or "sprayed" therefrom. Accordingly, an air-delivery lumen may be provided that extends from an air or gas source to the bladder 118. In an exemplary embodiment, the air-delivery lumen may be the fluid delivery lumen 119 or, alternatively, may comprise a separate and distinct lumen. When activated, the air source sends a stream of air to the bladder 118 with enough force to cause the fluid therein to spray out of, for example, the holes 124. In another exemplary embodiment, illustrated, for example, in FIG. 5, the bladder 118 includes one or more outlets 126 therein that are coupled to a fluid source, such as, for example, fluid source 102, through one or more fluid delivery lumens, such as, for example, lumen 119. In such an embodiment, when the fluid source 102 is activated, fluid is delivered directly to the outlet(s) 126 by the corresponding lumen(s) and is dispensed from the outlet to surrounding tissue. It will be appreciated that this particular embodiment may find application in embodiments of the probe 100 wherein the bladder 118 is inflated with gas or fluid.

In yet another exemplary embodiment, the bladder 118 is constructed of a fluid-permeable polymer that is configured to weep a film of fluid onto the outer surface of the bladder 118 when the bladder 118 is filled with fluid. In an exemplary embodiment, the polymer material may comprise, for example and without limitation, a porous urethane or a porous PEBAX®. It will be understood that the term "porous" as used herein is intended to mean permeable to fluid due to the presence of one or more apertures or holes, regardless of how or when the holes we formed in the bladder 118 (e.g., during manufacture of the bladder, or post manufacture by laser drilling or punching operations).

In any of the embodiments described above in which the bladder is configured to contact the wall of the esophagus and to expel or distribute fluid or gel onto the outer surface of the bladder 118 and/or surrounding esophageal tissue (or in an embodiment wherein the bladder 118 is pre-coated with a gel, for example), it may be desirable to maintain wetted contact between the bladder 118 and the tissue. Wetted contact assures low-resistance heat transfer across the bladder/tissue interface, and therefore, provides good heat-sinking capabilities. By distributing fluid and/or gel onto the outer surface of the bladder 118 and/or the surrounding tissue (or pre-coating the bladder 118 with gel), drying out of the interface as a result of the heat produced during the ablation procedure is substantially prevented. Additionally, in certain instances the bladder 118 may have folds, pleats, or creases as inflated against the wall of the esophagus. By distributing fluid or gel from the bladder 118, or by pre-coating the bladder with a gel, gaps between the bladder and the tissue caused by the folds, pleats, or creases can be filled to preserve thermal conductivity.

In each of these embodiments, because cooling fluid is dispensed from the bladder 118 onto the surrounding tissue, it may be that a certain margin of tolerance is permitted with respect to the positioning of the heat sink 110 directly opposite the ablating device 18, and the ablation element 30 thereof, in particular. It will be understood and appreciated that in some or all of these embodiments, the fluid dispensed from the bladder 118 will flow down the walls of the esophagus (presuming vertical orientation) protecting regions of non-targeted tissue even below the heat sink 110, and the bladder 118 thereof, in particular. The patient may also be oriented with gravity in a manner to assure that it is the heart-facing portion of the esophagus that is wetted by the fluid. Additionally, in an exemplary embodiment, the bladder 118 is configured to be many times larger in area than the size of the potential thermal esophageal fistula, and therefore, only crude accuracy in placement is required. However, in order to aid accuracy of placement of the bladder 118 (and/or the balloons 36,38 discussed above) one or more tracking or visualization elements can be coupled thereto or therein. For example, one or more magnets, coils or electrodes can be utilized that are MRI-, radio- or fluoro-opaque, or responsive or capable of being visualized with an impedance-based system such as the EnSite NavX™ system commercially available from St. Jude Medical, Inc. Additionally, a fluoroscopic contrast-bearing fluid may be distributed within or onto the outer surface of the bladder 118 to allow for fluoroscopic imaging of the bladder 118 to assist in bladder 118 placement.

As briefly described above, each of the above-described embodiments may be used to cool the tissue during the performance of an ablation procedure, or to pre-cool the non-targeted tissue in the region proximate to or wherein an ablation procedure is to be performed. In the latter instance, the bladder 118 may be used to cool the tissue with the fluid from the bladder 118 a certain amount, such as, for example, 5-20° C. below natural body (esophagus) temperature. This provides even more temperature safety margin before a thermal fistula can be formed.

Accordingly, in view of the above, it will be understood and appreciated that the esophagus, or at least portions thereof, may be thermally protected by abutting the bladder 118 against the esophagus wall, and/or by spraying, leaking, weeping or otherwise dispensing fluid from the bladder 118 and onto the surrounding tissue from a distance of zero to several millimeters between the bladder and the tissue. Therefore, it will be further understood and appreciated that the bladder may or may not physically touch the tissue in order to protect the tissue.

Figure 6:
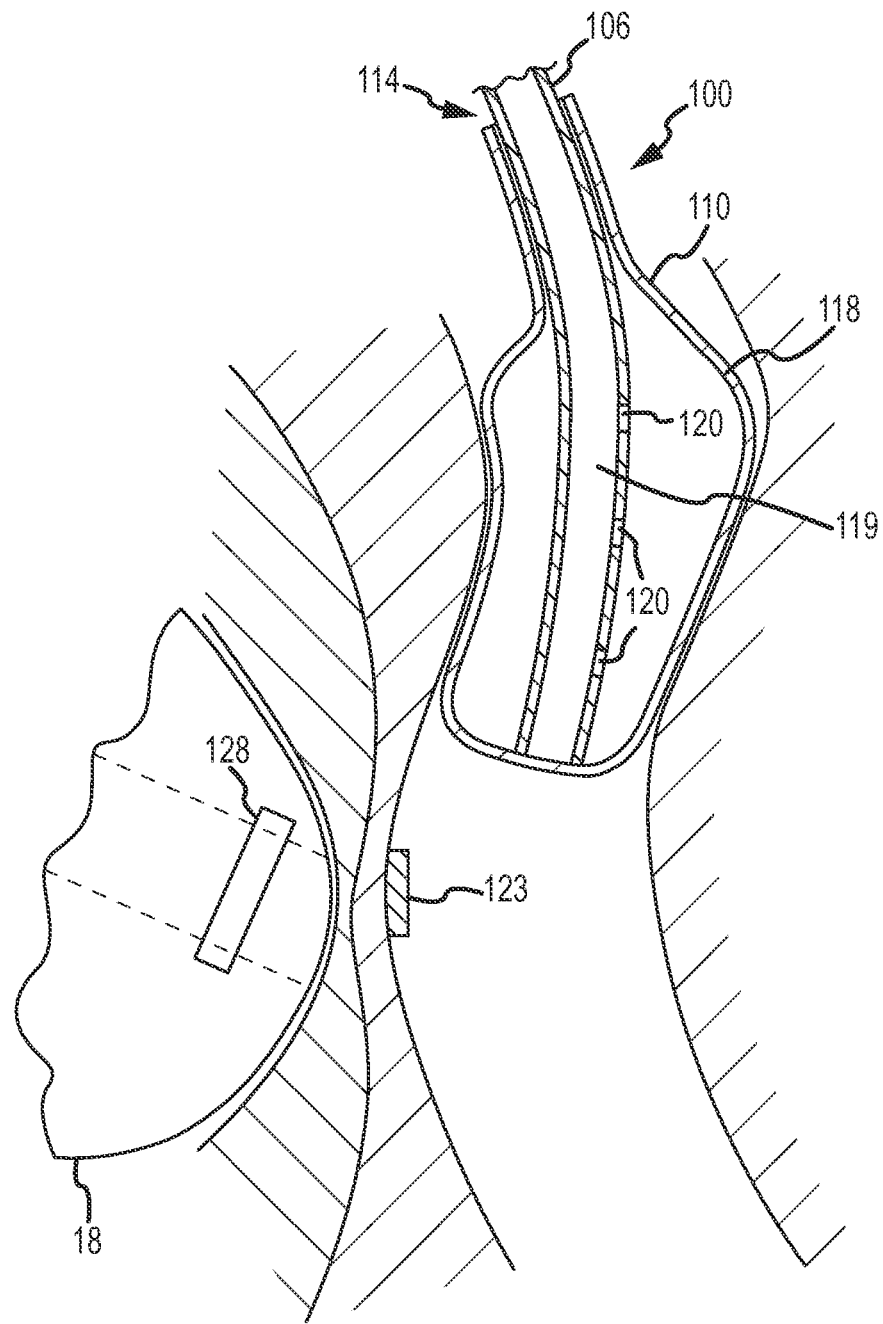
FIG. 6 is partial cross-section diagrammatic view of another exemplary embodiment of the probe of the temperature monitoring and/or management subsystem of the system illustrated in FIG. 1, wherein the probe is disposed within the esophagus of a patient, and further wherein the ablating device of the ablation system includes an acoustic transducer mounted thereon.
Figure 7:
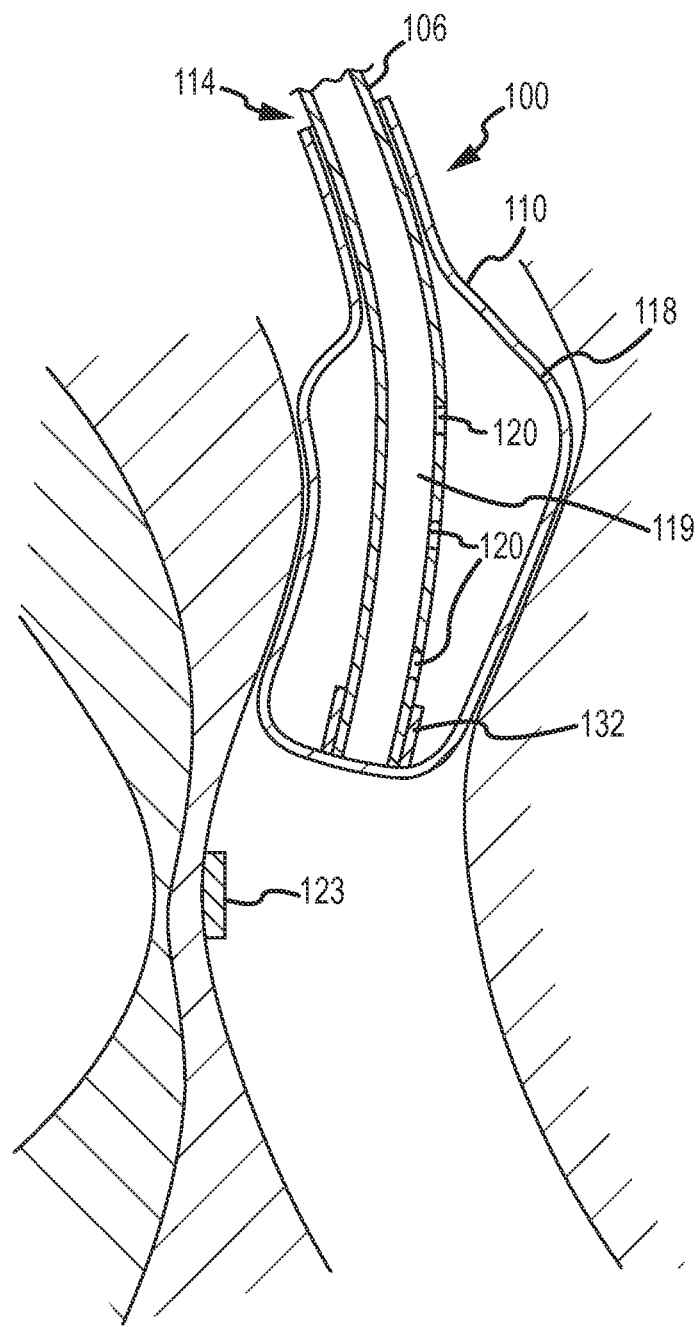
FIG. 7 is partial cross-section diagrammatic view of yet another exemplary embodiment of the probe of the temperature monitoring and/or management subsystem of the system illustrated in FIG. 1, wherein the probe is disposed within the esophagus of a patient, and further wherein an acoustic transducer is mounted at the distal end of the probe.
Figure 8:
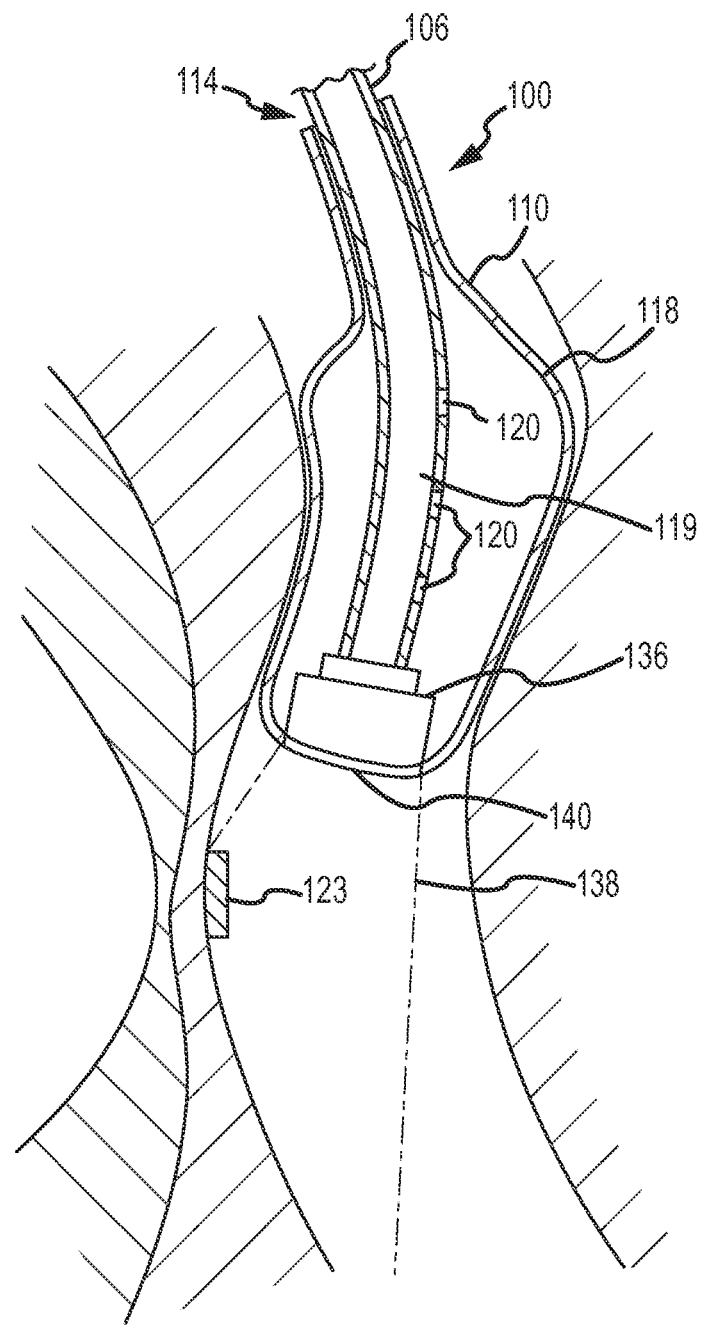
FIG. 8 is partial cross-section diagrammatic view of yet still another exemplary embodiment of the probe of the temperature monitoring and/or management subsystem of the system illustrated in FIG. 1, wherein the probe is disposed within the esophagus of a patient, and further wherein a thermal imaging chip is mounted at the distal end of the probe.

Turning now to FIGS. 6-8, in an exemplary embodiment, a means for ensuring the probe 100, and the tissue protecting apparatus 110 thereof, in particular, is positioned in close proximity to the ablation site, and therefore, the ablation element 30 of the ablating device 18, is provided. In an exemplary embodiment wherein the tissue protecting apparatus 110 does perform a heat sinking function, the degree of wetted or acoustic contact between the heat sink 110 and the tissue may also be determined. This locating and/or degree of contact functionality ensures that the tissue protecting apparatus 110 is positioned in an area in which hotspots are most likely to be generated, and it may be carried out in a number of ways.

In an exemplary embodiment, known imaging systems or modalities that allow the user of the system 10 to visually determine where the probe 100 is positioned, and to then confirm whether it is in an acceptable location, may be employed. One such imaging modality, which is provided for exemplary purposes only and not meant to be limiting in nature, is fluoroscopy. Fluoroscopy provides a real-time image of a region of interest of a patient's anatomy and medical devices disposed therein, and therefore, is a good imaging system for real-time probe location detection/confirmation. In an embodiment of the system 10 employing fluoroscopy, markers, such as radio opaque markers or other markers well known in the art, may be placed in or on the probe 100 and the tissue protecting apparatus 110, in particular, to allow for them to be visualized or imaged by the fluoroscopic imaging system. Alternatively, in an embodiment wherein the tissue protecting apparatus includes a fluid-inflatable bladder, the fluid within the bladder 118 may contain a fluoroscopic contrast agent or other imaging-modality contrast agent to allow the bladder 118 to be visualized using fluoroscopy or another imaging modality. Additionally, or alternatively, the material of the bladder 118 may itself be fluoroscopically visible. In any instance, this allows for the verification of bladder placement and inflation.

In another exemplary embodiment illustrated in FIG. 6, an acoustic transducer 128 electrically connected to circuitry associated with the system 10, such as, for example the ablating subsystem 12, the temperature monitoring and management subsystem 14, or the system controller 16, is mounted or otherwise disposed on the ablating device 18 in close proximity to the ablation element 30. In an exemplary embodiment, a processor 130 is also provided, which may be part of either the ablation subsystem 12, the temperature monitoring and management subsystem 14, or, as illustrated in FIG. 1, the system controller 16, and is electrically connected to the transducer 128.

The acoustic transducer 128 is configured to emit acoustic waves directed toward the ablation site, and therefore, in the direction of where the distal portion of the probe 100 should be located, to ping the probe 100, and preferably, the tissue protecting apparatus 110 thereof, in particular. The acoustic transducer 128 is further configured to receive a pulse-echo reflection of the signal and to communicate that signal to the processor 130. From the sent and received signals, the processor 130 can determine whether the probe 100 is properly positioned and/or whether there is a high degree of wetted or acoustic contact between the probe 100 and the tissue using methods well known in the art (e.g., a large reflection is indicative of an air-filled esophagus without the probe 100 (e.g., the bladder 118), and a much smaller reflection is indicative of the wet-coupled presence of the probe 100 (e.g., the bladder 118). Additionally, or alternatively, in an embodiment including the inflatable bladder 118, a microbubble contrast agent, such as, for example, a liposome-based material, may be put in the inflating fluid such that it can be acoustically recognized as a large reflector). This indication can then be provided to the practitioner performing the ablation procedure either audibly or visually, such as, for example, on a display monitor or through an audio indicator.

Additionally, or alternatively, in an exemplary embodiment wherein one or more focused ultrasonic ablators (e.g., HIFU ablator) is employed by the ablating subsystem 12, the ablator may be configured to acoustically detect, in a pinging mode similar to that described above, the acoustical/thermal contact of the opposed tissue protecting apparatus 110 and the tissue.

In still another exemplary embodiment illustrated, for example, in FIG. 7, the subsystem 14 includes an acoustic transducer 132 coupled with or mounted to the probe 100, preferably at the distal end 114 thereof (as opposed to the transducer being mounted to the ablating device). In an exemplary embodiment, a processor 134 is further provided and electrically connected to the transducer 132. The processor 134 may be part of the subsystem 14, or in other exemplary embodiments, part of the ablation subsystem 12 or the system controller 16 (as is illustrated in FIG. 1). The acoustic transducer 132 is configured to emit acoustic waves in the perceived direction of the ablation site, and therefore, in the direction of where the ablating device 18, and the ablation element 30 thereof, in particular, should be located, to ping or bounce low power energy off of the ablating device 18. The acoustic transducer 132 is further configured to receive a pulse-echo reflection of the signal and to communicate that signal to the processor 134. From the sent and received signals, the processor 134 can determine whether the probe 100 is properly positioned relative to the ablating device 18 using methods well known in the art (e.g., a weak return signal indicative of the ablating device 18 not being present, while a strong return signal indicative of proper, or at least close, placement of the probe 100 relative to the ablating device 18). This indication can then be provided to the practitioner performing the ablation procedure audibly and/or visually, for example. This particular embodiment provides the advantage that the "coupling" (e.g., thermal coupling) between the ablating device 18 and the probe 100 can be monitored throughout the performance of an ablation procedure without disrupting the operation of the ablating device 18.

In yet still another exemplary embodiment illustrated in FIG. 8, the subsystem 14 further includes a temperature monitoring apparatus at least a portion of which is coupled, mounted, otherwise disposed within or on the probe 100 at or near the distal end thereof. In an exemplary embodiment, the temperature monitoring apparatus includes a thermal imaging chip 136 that is mounted to the probe 100 proximate the distal end thereof. In another exemplary embodiment described below, the temperature monitoring apparatus comprises the thermal imaging chip 136 as well as an imaging fiber bundle electrically connected to said thermal imaging chip 136. In such an embodiment, a portion of the imaging fiber bundle is disposed proximate the distal end of the probe 100. In either embodiment, the temperature monitoring apparatus (e.g., the thermal imaging chip 136, for example) has a field of view 138 and is configured to generate an image or images of the tissue, such as, for example, esophageal tissue, disposed within the field of view 138. In an exemplary embodiment, the thermal imaging chip 136 is an infrared imaging chip, such as, for example, a mid-IR or long-IR wavelength infrared imaging chip, and is further configured to visually detect temperatures of the imaged tissue. In the illustrated embodiment, the tissue protecting apparatus 110 (i.e., the inflatable bladder and components thereof), is configured to act as a clamp of sorts to stabilize the position of the probe 100 to provide a desired line-of-sight for the thermal imaging chip 136.

In one exemplary embodiment, the tissue protecting apparatus 110 does not dispense fluid as described above, and, if the tissue protecting apparatus 110 includes an inflatable component, it may or may not be inflated with fluid. In another exemplary embodiment, however, wherein the tissue protecting apparatus 110 includes an inflatable bladder, such as, for example, bladder 118, in addition to stabilizing the position of the probe 100, the bladder 118 may be inflated with, and/or configured to dispense, fluid therefrom as described above. It will be understood by those having ordinary skill in the art that when using infrared thermography, such as, for example, those techniques identified above, it is the nearest surface of the tissue or surface of the fluid-covering the tissue that is being visualized or imaged. The surface temperature is thus being measured and not the potentially much hotter interstitial tissue of the targeted tissue, or for that matter, the non-targeted tissue. Additionally, in certain embodiments, the temperature monitoring apparatus, or at least a portion thereof, may be disposed within the fluid in the bladder 118. Accordingly, in such an embodiment, the fluid used to inflate and/or cool the tissue must be an infrared transparent (as opposed to opaque) fluid such that thermography works even through the fluid, and the temperature monitoring apparatus can look through or from within the fluid.

Additionally, in an exemplary embodiment, the thermal imaging chip 136 may have a lens or window 140, and the lens 140 may be warmed in order to prevent it from fogging so as to maximize the resolution and contrast of the images. Further, the thermal imaging chip 136 may include a protective covering (not shown) in case the thermal imaging chip 136 comes into contact with tissue.

In one exemplary embodiment, using known techniques, the temperature monitoring apparatus is configured to determine the highest temperature in the imaged tissue, and to communicate the same to a processor 142 (shown in FIG. 1) or other circuitry associated with subsystem 14 (or the ablation subsystem 12 or the system controller 16). The processor 142 is configured, at least in part, to compare the determined highest temperature or a too-rapid time rate of change measured surface temperature with a predetermined threshold temperature or rate of change, and to provide the practitioner performing the ablation procedure an audible and or visual warning if the measured highest temperature approaches or reaches the predetermined threshold (e.g., a temperature at or near the highest temperature at which burning or damage to the esophageal tissue is not expected to occur, or a predetermined rate of change threshold). For example, the subsystem 14 may further include an alarm system controllable by, for example, the processor 142, to provide an audible and/or haptic warning that the threshold has been met or is being approached, and/or a display monitor 144 (best shown in FIG. 1) controllable by, for example, the processor 142, to display the imaged tissue, as well as a visual warning that the threshold has been met or is being approached. This information may be further communicated to the system controller 16, for example, or to ablation subsystem 12, which may then cause the ablating device 18 to be turned "off" or turned "down" in order to prevent or mitigate burning in the esophageal tissue, for example, or to take other corrective or mitigating actions. The detected thermal hotspot may also be used to predict the temperature trajectory and have the system undertake preventative or warning actions, and/or to control the ablative energy level. In an exemplary embodiment, low energy may be delivered by the ablating device 18 for purposes of estimating how hot the esophageal tissue will get at higher ablation energy.

In an exemplary embodiment, the predetermined temperature/rate of change threshold may be adjustable so as to allow for the adjustment of the sensitivity of the system. In such an embodiment, the subsystem 14 may include a conventional user input device electrically coupled to, and configured for communication with, the processor 142 to allow for the adjustment of the threshold. Accordingly, in such an embodiment, the processor 142 may be preprogrammed with an initial threshold, and then reprogrammed to adjust the threshold, or may be programmable. Alternatively, the predetermined threshold may be a preprogrammed and fixed value that may not be adjusted.

Figure 9:
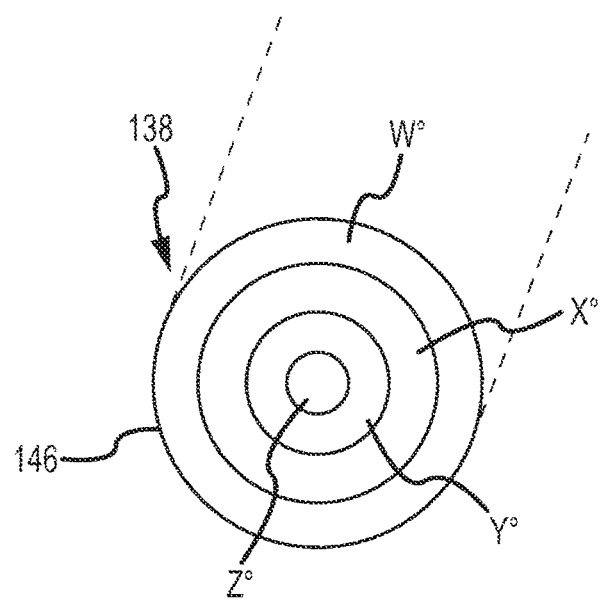
FIG. 9 is a graphical representation of a thermographic map generated by the thermal imaging chip illustrated in FIG. 8.

In another exemplary embodiment, the thermal imaging chip 136, and/or other circuitry of the temperature monitoring apparatus or subsystem 14, such as, for example and without limitation, the processor 142, may be configured to generate a thermographic map 146 of the imaged tissue (best shown in FIG. 9). The thermographic map 146 depicts the temperature of various areas of the imaged tissue. In such an embodiment, the display monitor 144 may be configured to display and/or store a temporal representation of the generated thermographic map 146. The thermographic map may be color coded by temperature, or may provide other indicators of the respective detected and depicted temperatures.

As briefly described above, in addition to the thermal imaging chip 136, in an exemplary embodiment the temperature monitoring apparatus may also include an imaging fiber bundle that is electrically connected to the thermal imaging chip 136. In such an embodiment, rather than or in addition to the imaging chip 136 being inserted into the patient's anatomy, the imaging fiber bundle is inserted into the patient's body. Because the imaging fiber bundle is electrically connected to the thermal imaging chip 136, the thermal imaging chip 136 is optically coupled to the interior anatomical site with the image fiber bundle. In this embodiment, the imaging chip 136 may be disposed, for example, within the probe 100, in the handle 108 thereof, or elsewhere within the temperature management and monitoring subsystem 14.

In another exemplary embodiment, rather than incorporating both the tissue protecting apparatus 110 and the temperature monitoring apparatus, the probe 100 may only include the temperature monitoring apparatus disposed at the distal end 114 thereof. In such an embodiment, the description set forth above relating to the temperature monitoring apparatus and its functionality applies here with equal force, and therefore, will not be repeated. Additionally, it will be appreciated that while in one exemplary embodiment, the probe 100 may be passed down the throat of the patient by itself, in another exemplary embodiment the probe 100 may be used in conjunction with a sheath.

Advantages offered by the use of the thermal imaging chip 136 include the ability to display the entire temperature map of the imaged tissue without having to perform any interpolation, which is required in physical thermistor arrays. Additionally, there are generally no loss-of-contact issues as the chip provides a visual image as opposed to taking measurements of the surface of the tissue itself. Finally, a wide view of a passageway, such as, for example, the esophagus can be achieved without having to move the probe once it is properly positioned.

Figure 10:
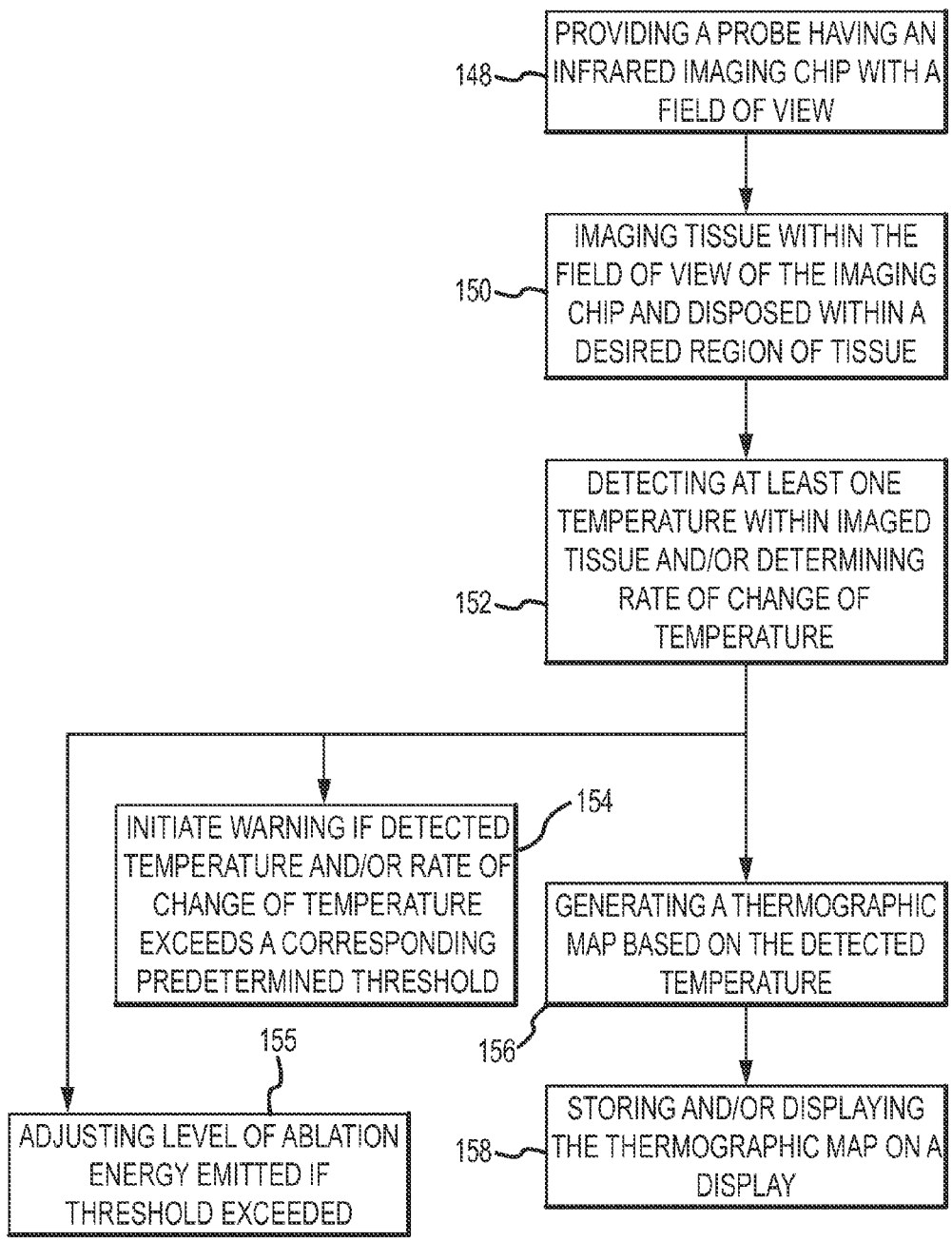
FIG. 10 is a flow diagram of an exemplary method of monitoring the temperature in a region of non-targeted tissue during an ablation procedure being performed on targeted tissue disposed proximate the desired region of non-targeted tissue.

With reference to FIG. 10, an exemplary method of monitoring temperature in a region of non-targeted tissue during an ablation procedure performed on targeted tissue proximate the non-targeted region of tissue will be described. In a first step 148, a probe including a temperature monitoring apparatus with a field of view 138 is provided. In a second step 150, tissue within the field of view 138 and also disposed within the desired region of tissue is imaged by the temperature monitoring apparatus (e.g., the imaging chip 136). In a third step 152, at least one temperature within the imaged tissue is determined. In an exemplary embodiment, step 152 comprises detecting the highest temperature in the imaged tissue, and fourth step 154 comprises initiating a warning if the detected highest temperature exceeds a predetermined threshold. Alternatively, a warning may be provided if the temperature is approaching the threshold temperature or if it is anticipated that the temperature threshold will be exceeded. In another exemplary embodiment, step 152 comprises determining a rate of change of the temperature in the tissue, and fourth step 154 comprises initiating a warning if the determined rate of change exceeds a predetermined threshold. Alternatively, a warning may be provided if the rate of change is approaching the threshold or if it is anticipated that the threshold will be exceeded. Still further, other actions in addition to, or instead of, providing a warning may be carried out. For example, a step 155 includes throttling or gating the ablation energy being applied by the ablating device to reduce or stop the application of ablation energy.

In another exemplary embodiment, step 152 comprises detecting a plurality of temperatures in the imaged tissue, and a subsequent step 156 includes generating a thermographic map corresponding to the detected plurality of temperatures. In a still further subsequent step 158, the generated thermographic map is displayed on a display monitor and/or stored in a storage medium.

The following examples of various embodiments of the invention, and/or further and other aspects of the invention, are provided for illustrative purposes and are not meant to be limiting in nature.

Example (1)

A system for performing an ablation procedure, comprising: an ablation subsystem including a thermal ablation device configured to be inserted into the anatomy of a patient and to deliver thermally heating ablating energy to a target ablation site; and a temperature monitoring and management subsystem including a protective probe configured to be inserted into the anatomy of said patient and positioned in close proximity to a region of non-targeted tissue proximate said targeted ablation site at a second site to be protected from said nearby ablation, said probe including a heat sink comprising a balloon, membrane or bladder (collectively referred to as "bladder") disposed at a distal portion of said probe and configured to be inflated or flushed with a cooling or heat-extracting fluid; and a fluid source configured to be coupled to said bladder and to supply fluid to said bladder; said heat sink of said temperature monitoring and management subsystem configured to transfer or remove heat generated or deposited in tissue in said region of non-targeted tissue by said ablating device such that it is not ablated. The bladder may also be coated with a hydrophilic gel or coating.

Example (2)

The system of example (1) wherein tissue in said region of non-targeted tissue is also pre-cooled below its natural body temperature by said bladder or heat sink thereby providing additional protection from unintended ablation.

Example (3)

The system of example (1) wherein said ablating device is configured to be inserted into the heart of a patient and said probe is configured to be inserted into the esophagus of said patient, and wherein the target ablation site is an endocardial tissue in a heart wall, and said second site is a nearby esophageal portion.

Example (4)

The system of example (3) wherein the ablating device is meant to ablate at least a portion of a pulmonary artery or ostium thereof.

Example (5)

The system of example (1) wherein the ablating device utilizes any one or more of radio frequency (RF), microwave, laser, or ultrasound ablation energy.

Example (6)

The system of example (1), further comprising a system controller electrically connected to said ablation subsystem and said temperature monitoring and management subsystem.

Example (7)

The system of example (1) further comprising a temperature monitor or temperature controller which is capable of at-least detecting a temperature of a tissue, a heat sink or a heat sinking fluid.

Example (8)

The system of example (1) wherein said bladder has an outer surface and said outer surface is lined with a thin film metallic material and/or a hydrophilic coating.

Example (9)

The system of example (1) wherein said bladder includes a plurality of microscopic holes or permeable paths therein to allow fluid in said bladder to flow or permeate out of said bladder to the outer surface of the bladder.

Example (10)

The system of example (1) wherein said bladder is constructed of a water permeable polymer configured to weep a film of fluid onto the outer surface of said bladder when said bladder is filled with fluid.

Example (11)

The system of example (1) wherein said bladder is designed to be hydrophilic or water-wettable regardless of whether fluid is delivered to the bladder surface from the bladder interior.

Example (12)

The apparatus of example (1) wherein said bladder includes at least one outlet therein configured to allow fluid to be sprayed, sheeted or dripped therefrom upon or across a protectable tissue surface.

Example (13)

The system of example (1) wherein said ablating device includes an acoustic transducer mounted thereon, said acoustic transducer electrically connected to a processor, and further wherein said acoustic transducer and said processor are configured to determine a location and/or a degree-of-contact of said probe relative to esophageal tissue.

Example (14)

The system of example (13) wherein said acoustic transducer is configured to transmit an acoustic signal and to receive a reflected acoustic signal corresponding to said transmitted acoustic signal reflected by said probe, said processor configured to process said transmitted and received acoustic signals and to determine said relative location of said probe or how well said probe is acoustically and therefore thermally coupled to the esophagus. A low acoustic reflection is indicative of a good thermally conducting wetted interface between the bladder and the tissue.

Example (15)

The system of example (1) wherein said probe further includes an acoustic transducer mounted thereon, said acoustic transducer electrically connected to a processor, and further wherein said acoustic transducer and said processor are configured to determine a location of said probe relative to said region of non-targeted tissue.

Example (16)

The system of example (15) wherein said acoustic transducer is configured to transmit an acoustic signal toward said region of non-targeted tissue and to receive a reflected acoustic signal corresponding to said transmitted acoustic signal reflected by tissue in said region of non-targeted tissue, said processor configured to process said transmitted and received acoustic signals to determine said relative location of said probe.

Example (17)

The system of example (1) wherein said probe further includes an thermal imaging chip mounted thereon, said thermal imaging chip having a field of view and configured to generate a thermal image of tissue in said region of non-targeted tissue that is disposed within said field of view, said imaging chip further configured to detect temperatures of said imaged tissue.

Example (18)

The system of example (17) wherein said thermal imaging chip is configured to generate a thermographic map corresponding said imaged tissue.

Example (19)

The system of example (18), further comprising a display monitor electrically connected to said imaging chip and configured to display said thermographic map.

Example (20)

The system of example (17) wherein said thermal imaging chip is configured to detect the highest temperature in said imaged tissue or in a fluid film on said tissue.

Example (21)

The system of example (17) wherein said bladder is operative to act as a clamp to stabilize a position of said imaging chip to provide a desired line-of-sight for said imaging chip.

Example (22)

A system for monitoring temperature in a region of non-targeted tissue not to be ablated during an ablation procedure performed on tissue proximate said region of non-targeted tissue, comprising a probe including an elongate shaft having a proximal end, a distal end, and an inflation or filling lumen disposed therein, said elongate shaft defining a longitudinal axis extending from said proximal end through said distal end; a handle disposed at said distal end; and a heat sink, wherein said heat sink comprises a bladder disposed at said distal end of said elongate shaft and extending therefrom a predetermined distance along said longitudinal axis of said elongate shaft toward said proximal end of said elongate shaft, wherein said bladder is configured to be filled with a fluid; a fluid source, wherein said inflation or filling lumen of said elongate shaft is coupled between and to each of said fluid source and said bladder, and said fluid source is configured to supply fluid to said bladder through said inflation or filling lumen; and an actuator configured to cause said balloon to be filled, emptied, flushed with fresh replacement fluid through its interior, or to emit fluid from at least one orifice or pore in its surface.

Example (23)

The system of example (22) wherein said actuator is mounted on or in said handle of said probe.

Example (24)

The system of example (22) wherein said actuator is associated with said fluid source.

Example (25)

The system of example (22) wherein said bladder has an outer surface and said outer surface is lined with a thin film metallic material and/or has a hydrophilic coating thereon.

Example (26)

The system of example (22) wherein said bladder includes a plurality of microscopic holes, pores, or permeable paths therein to allow fluid in said bladder to flow out of said bladder.

Example (27)

The system of example (22) wherein said bladder is constructed of a water permeable polymer configured to weep a film of fluid on the outer surface of said bladder when said bladder is filled with fluid.

Example (28)

The apparatus of example (22) wherein said bladder includes at least one outlet therein configured to allow fluid to be sprayed, sheeted or dripped therefrom across the surface of a protectable tissue.

Example (29)

The system of example (22) wherein said heat sink further includes a return lumen disposed between, and in fluid communication with, said bladder and said fluid source, said return lumen configured to return fluid from said bladder to said fluid source or to a patient-external drain.

Example (30)

The system of example (22), further comprising an acoustic transducer mounted on an ablating device performing said ablation procedure, said acoustic transducer electrically connected to a processor, and said acoustic transducer and said processor configured to determine a location of said probe relative to said ablating device or to determine a degree of wetted or acoustic coupling between said probe and said tissue. The ablation device in this example may be a HIFU ablation device wherein the HIFU ablation and pinging are both done by the same transducer.

Example (31)

The system of example (30) wherein said acoustic transducer is configured to transmit an acoustic signal and to receive a reflected acoustic signal corresponding to said transmitted acoustic signal reflected by said probe, said processor configured to process said transmitted and received acoustic signals and to determine said relative location of said probe or to determine a degree of wetted or acoustic coupling between said probe and said tissue.

Example (32)

The system of example (22), further comprising an acoustic transducer mounted to said elongate shaft of said probe proximate said distal end thereof and electrically connected to a processor, said ultrasound transducer and said processor configured to determine a location of said probe relative to said region of non-targeted tissue or to determine a degree of wetted or acoustic coupling between said probe and said tissue.

Example (33)

The system of example (22) wherein said acoustic transducer is configured to transmit an acoustic signal toward said region of non-targeted tissue and to receive a reflected acoustic signal corresponding to said transmitted acoustic signal reflected by tissue in said region of non-targeted tissue, said processor configured to process said transmitted and received acoustic signals to determine said relative location of said probe or to determine a degree of coupling between said probe and said tissue.

Example (34)

The system of example (22), further comprising an thermal imaging chip mounted to said elongate shaft of said probe proximate said distal end thereof, said thermal imaging chip having a field of view and configured to generate an image of tissue in said region of non-targeted tissue disposed within said field of view, said imaging chip further configured to detect temperatures of said imaged tissue.

Example (35)

The system of example (34) wherein said imaging chip is configured to generate a thermographic map corresponding said imaged tissue.

Example (36)

The system of example (35), further comprising a display monitor connected to said thermal imaging chip and configured to display said thermographic map.

Example (37)

The system of example (34) wherein said thermal imaging chip or supportive software analyzing the image is configured to detect the highest temperature in said imaged tissue.

Example (38)

The system of example (34) wherein said bladder is operative to act as a clamp to stabilize a position of said thermal imaging chip to provide a desired line-of-sight for said imaging chip.

Example (39)

An apparatus for use in monitoring and/or managing temperature in a region of non-targeted tissue during an ablation procedure performed proximate said region of non-targeted tissue, comprising an elongate shaft having a proximal end, a distal end, and an inflation lumen disposed therein, said elongate shaft defining a longitudinal axis extending from said proximal end through said distal end; a handle disposed at said proximal end; a heat sink, wherein said heat sink assembly comprises a bladder disposed at said distal end of said elongate shaft and extending therefrom a predetermined distance along said longitudinal axis of said elongate shaft toward said proximal end of said elongate shaft, said bladder coupled with said inflating lumen and configured to be filled with a heat-transfer or cooling fluid supplied by a fluid source to which said bladder is coupled; and an actuator or valve configured to cause said bladder to be at least partially filled or emptied of fluid and preferably to also weep or spray fluid from its surface upon or across tissue.

Example (40)

The apparatus of example (39) wherein said bladder has an outer surface and said outer surface is lined with a thin film metallic material and/or a hydrophilic coating.

Example (41)

The apparatus of example (39) wherein said bladder includes a plurality of microscopic holes, pores, or permeable paths therein to allow fluid in said bladder to flow out of said bladder at least to the outer surface of the bladder.

Example (42)

The apparatus of example (39) wherein said bladder is constructed of a water permeable polymer configured to weep or permeate a film of fluid on or onto the outer surface of said bladder when said bladder is filled with fluid.

Example (43)

The apparatus of example (39) wherein said bladder includes at least one outlet or orifice therein configured to allow fluid to be sprayed, sheeted or dripped therefrom.

Example (44)

The apparatus of example (39) wherein said heat sink further includes a return lumen disposed between, and in fluid communication with, said bladder and said fluid source, said return lumen configured to return fluid from said bladder to said fluid source or to a patient-external drain.

Example (45)

The apparatus of example (39), further comprising an acoustic transducer mounted to said elongate shaft proximate said distal end thereof and electrically connected to a processor, said ultrasound transducer and said processor configured to determine a location of said apparatus relative to said region of non-targeted tissue or to determine a degree of wetted or acoustic coupling between said probe and said tissue.

Example (46)

The apparatus of example (45) wherein said acoustic transducer is configured to transmit an acoustic signal toward said region of non-targeted tissue and to receive a reflected acoustic signal corresponding to said transmitted acoustic signal, and said processor is configured to process said transmitted and received acoustic signals to determine said relative location of said apparatus or to determine a degree of wetted or acoustic coupling between said probe and said tissue.

Example (47)

The apparatus of example (39), further comprising a thermal imaging chip mounted to said elongate shaft proximate said distal end thereof, said thermal imaging chip having a field of view and configured to generate an image of tissue in said region of non-targeted tissue disposed within said field of view, said imaging chip further configured to detect temperatures of said imaged tissue.

Example (48)

The apparatus of example (47) wherein said thermal imaging chip is configured to generate a thermographic map corresponding said imaged tissue.

Example (49)

The apparatus of example (47) wherein said thermal imaging chip or supportive software is configured to detect the highest temperature in said imaged tissue.

Example (50)

The apparatus of example (47) wherein said bladder is operative to act as a clamp to stabilize a position of said imaging chip to provide a desired line-of-sight for said imaging chip.

Example (51)

An apparatus for use in monitoring temperature in a region of non-targeted tissue during an ablation procedure performed on targeted tissue proximate said region of non-targeted tissue, comprising: a probe having a proximal end and a distal end; and an infrared thermal imaging chip mounted to said probe proximate said distal end thereof; wherein said thermal imaging chip has a field of view and is configured to generate an image of tissue in said region of non-targeted tissue disposed within said field of view, and further wherein said imaging chip, or supportive software working with the image, is configured to detect temperatures of said imaged tissue.

Example (52)

The apparatus of example (51) wherein at least a portion of said probe containing said thermal imaging chip is configured to be disposed within the body of a patient.

Example (53)

The apparatus of example (51) wherein at least a portion of said probe containing said thermal imaging chip is configured to be disposed outside of the body of a patient.

Example (54)

The apparatus of example (51) wherein said thermal imaging chip is configured to generate a thermographic map corresponding said imaged tissue.

Example (55)

The apparatus of example (54), further comprising a display monitor connected to said thermal imaging chip and configured to display said thermographic map.

Example (56)

The apparatus of example (51) wherein said thermal imaging chip or software used to analyze the image is configured to detect the highest temperature in said imaged tissue.

Example (57)

The apparatus of example (51), wherein said probe further comprises an inflatable clamp mounted thereon to stabilize a position of said thermal imaging chip when inflated to provide a desired line-of-sight for said imaging chip.

Example (58)

The apparatus of example (51) wherein said imaging chip is a CCD chip which may optionally also have visible-wavelength imaging capabilities.

Example (59)

The apparatus of example (51) wherein said imaging chip is a CMOS chip which may optionally also have visible-wavelength imaging capabilities.

Example (60)

A method of monitoring temperature in a region of non-targeted tissue during an ablation procedure performed on targeted tissue proximate said region of non-targeted tissue, said method comprising: providing a probe including an infrared thermal imaging chip having a field of view; imaging tissue within said field of view of said thermal imaging chip and disposed within said region of non-targeted tissue; and detecting at least one temperature of said imaged tissue.

Example (61)

The method of example (60) wherein said detecting step comprises detecting the highest temperature in said imaged tissue.

Example (62)

The method of example (61), further comprising the step of initiating a warning or throttling/gating ablation power if said detected highest temperature exceeds or is anticipated to exceed a predetermined threshold.

Example (63)

The method of example (60) wherein said detecting step comprises detecting a plurality of temperatures in said imaged tissue.

Example (64)

The method of example (63), further comprising the step of generating a thermographic map corresponding to said detected plurality of temperatures.

Example (65)

The method of example (64), further comprising the step of displaying said thermographic map on a display monitor.

Example (66)

An ablating device, comprising an elongate shaft having a proximal end and a distal end; a handle mounted to said elongate shaft at said proximal end thereof; and an ablation element mounted to said elongate shaft at said distal end, said ablation element including an ultrasound transducer and at least one inflatable balloon surrounding said ultrasound transducer, and wherein said balloon having an inner surface and an outer surface, and said balloon further having a layer of semisolid gel or hydrophilic coating disposed on at least a portion of said outer surface at-least during ablative operation. The gel or hydrophilic coating allowing for an external balloon surface to provide a reliable flow-seal against blood flow during an ablation procedure.

Example (67)

The ablation device of example (66) wherein said gel or coating is configured to become more solid or less flowable when heated or while warmed.

Example (68)

The ablation device of example (67) wherein said gel or coating is configured to become more flowable or more liquid-like when cooled from at least one higher temperature to at least one lower temperature.

Example (69)

The ablation device of example (67), further comprising a heating or cooling device configured to apply or remove heat to/from said gel or coating in order to change its degree of solidity or flowability.

Example (70)

The ablation device of example (66) wherein the gel or coating is introduced into the device as a flowable liquid, is thermally rendered semisolid or poorly flowable during ablation, and is thereupon thermally rendered again flowable after ablation.

Example (71)

The ablation device of example (66) wherein said at least a portion of said outer surface of said balloon is coated with said gel or hydrophilic coating material prior to said elongate shaft being inserted into a patient, and/or by passage of gel or coating material from inside the balloon through the balloon wall to the outer balloon surface.

Example (72)

The ablation device of example (71) wherein said gel or coating material is distributed onto said at least a portion of said outer surface of said balloon after said balloon is inflated.

Example (73)

The ablation device of example (72) wherein said balloon further includes at least one port disposed therein configured to distribute said gel or coating material onto said at least a portion of said outer surface of said balloon.

Example (74)

The ablation device of example (73), further comprising a gel or coating distribution lumen disposed in said elongate shaft and extending from said proximal end to said distal end, said lumen being coupled to said port and configured to communicate said liquefying gel or coating material from a source to said port.

Example (75)

A method of ablating pulmonary vein ostia or any portion of a myocardium while thermally protecting a nearby esophagus from ablation comprising: a thermal ablation device operable from within the heart to ablate one or more ostia, myocardial tissues, or portions thereof; a heat sinking protective probe insertable down an esophagus to thermally couple to esophageal tissues to be protected from ablation taking place nearby in the heart; wherein at least one of (a) the heat sinking probe pre-cools the protectable esophageal tissues thereby providing increased thermal margin for ablation protection of those protected tissues; and (b) the heat sinking probe acts to sink away heat for potential undesirable hotspots developed in the esophagus by the nearby thermal ablator.

Example (76)

The method of example (75) wherein any one or more of: (a) the heat sinking probe utilizes a thermally conductive fluid or utilizes a circulated fluid; (b) the heat sinking probe utilizes a fluid inflatable balloon, membrane or bladder; (c) the heat sinking probe is inflated at least partially against interior esophageal tissues; (d) the heat sinking probe is rendered hydrophilic or water wettable on its external surface during manufacturing or during use; (e) the thermal ablator is any one of an RF, microwave, laser, cryogenic or ultrasonic ablator; and (f) the heat sinking probe sprays, weeps, sheets, or drips fluid across or upon an esophageal tissue to be protected.

Example (77)

In any of the above examples, the transducer of the ablation element may be rotated during an ablation procedure to counteract an angular non-uniformity of the transducer output via rotational averaging. This is particularly applicable to a non-uniform 360 degree piezotube which benefits from rotation or to a sector transducer of less than 360 degrees which must be rotated.

Although only certain embodiments of this invention have been described above with a certain degree of particularity, those skilled in the art could make numerous alterations to the disclosed embodiments without departing from the scope of this invention. For example, various types of gel and many different gel dispensing techniques may be used to prevent blood leakage during an ablation procedure, and the gel may be distributed onto the outer surface of one or more of the balloon(s) in a number of ways. Further, the heat sink of the temperature monitoring and management subsystem may be inflated, and also cool proximate tissue, in any number of ways. Still further, the determination of the location of the probe of the temperature monitoring subsystem may be accomplished using various other methodologies or techniques. Additionally, any and all directional references (e.g., up, down, left, right) are only used for identification purposes to aid the reader's understanding of the present invention, and do not create limitations, particularly as to the position, orientation, or use of the invention. Joinder references (e.g., attached, coupled, connected, mounted and the like) are to be construed broadly and may include intermediate members between a connection of elements and relative movement between elements. As such, joinder references do not necessarily infer that two elements are directly connected/coupled and in fixed relation to each other. It is intended that all matter contained in the above description or shown in the accompanying drawings shall be interpreted as illustrative only and not limiting. Changes in detail or structure may be made without departing from the invention as defined in the appended claims.

What is claimed is:

1. A system for performing an ablation procedure, comprising:
 an ablating device configured to be inserted into the anatomy of a patient and to deliver ablating energy to an ablation site having targeted tissue;
 a probe configured to be inserted into the anatomy of said patient and to be positioned proximate a region of non-targeted tissue that is proximate said ablation site, said probe comprising a tissue protecting apparatus disposed at a distal portion of said probe and configured to protect tissue in said region of non-targeted tissue from unintended ablation from said ablating device, said probe further comprising a fluid distribution lumen enabling said tissue protecting apparatus to receive fluid from a fluid source; and
 a processor configured to determine contact and a degree of coupling between said tissue protecting apparatus and tissue in said region of non-targeted tissue that is proximate said ablation site; and wherein:
  (a) the system further comprises a fluid flow controller configured to control the fluid source to create a circulation of fluid in said tissue protecting apparatus during the delivery of ablating energy; and
  (b) said tissue protecting apparatus comprises one or more fluid outlets configured to allow fluid to exit said tissue protecting apparatus onto said region of non-targeted tissue.

2. The system of claim 1 wherein said ablating device is configured to be inserted into the heart of a patient and said probe is configured to be inserted into the esophagus of said patient.

3. The system of claim 1, further comprising:
 an acoustic transducer mounted on one of said probe and said ablating device.

4. The system of claim 1 further comprising a temperature monitoring apparatus mounted to said probe configured to monitor the temperature of said region of non-targeted tissue.

5. The system of claim 1, wherein said probe comprises:
 an elongate shaft having a proximal end portion and a distal end portion; and
 a handle disposed at said proximal end;
 wherein said tissue protecting apparatus is disposed at said distal end portion of said elongate shaft.

6. The system of claim 1, wherein said ablating device comprises:
 an elongate shaft having a proximal end portion and a distal end portion;
 a handle disposed at said proximal end portion; and
 a component for delivering ablation energy disposed at said distal end portion of said shaft.

7. The system of claim 1, wherein said ablating device comprises a first elongate shaft, said first elongate shaft having a distal end portion, and an ablation energy delivery component, said ablation energy delivery component disposed at said distal end portion of said first elongate shaft;
 further wherein said probe comprises a second elongate shaft that is separate from said first elongate shaft, said second elongate shaft having a distal end portion, said tissue protecting apparatus disposed at said distal end portion of said second elongate shaft.

8. The system of claim 1, wherein said probe comprises a handle and said fluid flow controller is mounted on said handle.

9. The system of claim 1, wherein said tissue protecting apparatus comprises a balloon and said one or more outlets comprise one or more holes in said balloon through which fluid may be dispensed from the balloon.

10. The system of claim 1 wherein said tissue protecting apparatus is a heat sink configured to reduce heat in said region of non-targeted tissue.

11. The system of claim 10, further comprising the fluid source, said fluid source configured to be coupled to said heat sink through said fluid distribution lumen, said fluid source configured to supply fluid to said heat sink through said fluid distribution lumen.

12. The system of claim 11 wherein said heat sink comprises one or more fluid outlets configured to allow fluid to exit said probe towards said region of non-targeted tissue.

13. The system of claim 11 wherein said heat sink comprises an inflatable bladder configured to be inflated with fluid from said fluid source.

14. A system for performing an ablation procedure, comprising:
    an ablating device configured to be inserted into the anatomy of a patient and to deliver ablating energy to an ablation site having targeted tissue;
    a probe configured to be inserted into the anatomy of said patient and to be positioned proximate a region of non-targeted tissue proximate said ablation site, said probe including a tissue protecting apparatus disposed at a distal portion thereof configured to protect tissue in said region of non-targeted tissue from unintended ablation from said ablating device; and
    a processor and an acoustic transducer electrically connected to said processor, wherein said acoustic transducer is mounted on one of said probe and said ablating device, and further wherein said processor is configured to receive information obtained with said acoustic transducer and to determine contact and a degree of coupling between said tissue protecting apparatus and tissue in said region of non-targeted tissue according to said information obtained with said acoustic transducer; and wherein:
        (a) the system further comprises a fluid flow controller configured to control the fluid source to create a circulation of fluid in said tissue protecting apparatus during the delivery of ablating energy; and
        (b) said tissue protecting apparatus comprises one or more fluid outlets configured to allow fluid to exit said tissue protecting apparatus onto said region of non-targeted tissue.

15. The system of claim 14, wherein said acoustic transducer and said processor are configured to determine a location of said probe.

16. The system of claim 14, wherein said ablating device is configured to be inserted into the heart of a patient and said probe is configured to be inserted into the esophagus of said patient.

17. The system of claim 14 further comprising a temperature monitoring apparatus mounted to said probe configured to monitor the temperature of said region of non-targeted tissue.

18. The system of claim 14, wherein said ablating device comprises:
    an elongate shaft having a proximal end portion and a distal end portion;
    a handle disposed at said proximal end portion; and
    a component for delivering ablation energy disposed at said distal end portion of said shaft.

19. The system of claim 14, wherein said ablating device comprises a first elongate shaft, said first elongate shaft having a distal end portion, and an ablation energy delivery component, said ablation energy delivery component disposed at said distal end portion of said first elongate shaft;
    further wherein said probe comprises a second elongate shaft that is separate from said first elongate shaft, said second elongate shaft having a distal end portion, said tissue protecting apparatus disposed at said distal end portion of said second elongate shaft.

20. The system of claim 14 wherein said tissue protecting apparatus is a heat sink configured to reduce heat in said region of non-targeted tissue.

21. The system of claim 20, further comprising a fluid source configured to be coupled to said heat sink through a fluid distribution lumen disposed within said probe, said fluid source configured to supply fluid to said heat sink through said fluid distribution lumen.

22. The system of claim 21 wherein said heat sink is configured to dispense fluid therefrom and onto tissue in said region of non-targeted tissue.

23. The system of claim 21 wherein said heat sink comprises an inflatable bladder configured to be inflated with fluid from said fluid source.

24. A method comprising:
    providing an acoustic transducer, the acoustic transducer mounted on:
        an ablating device configured to be inserted into the anatomy of a patient and to deliver ablating energy to an ablation site having targeted tissue; or
        a probe configured to be inserted into the anatomy of a patient and to be positioned proximate a region of non-targeted tissue proximate an ablation site, the probe including a tissue protecting apparatus disposed at a distal portion thereof configured to protect tissue in the region of non-targeted tissue from unintended ablation from an ablating device;
    receiving, with a processor, information from the acoustic transducer;
    determining, with the processor, contact and a degree of coupling between said tissue protecting apparatus and tissue in said region of non-targeted tissue according to the information received from the acoustic transducer;
    providing a fluid flow controller configured to control the fluid source to create a circulation of fluid in said tissue protecting apparatus during the delivery of ablating energy; and
    wherein said tissue protecting apparatus comprises one or more fluid outlets configured to allow fluid to exit said tissue protecting apparatus onto said region of non-targeted tissue.

25. The method of claim 24, further comprising determining, with the processor, a location of the probe according to the information received from the acoustic transducer.

* * * * *